(12) United States Patent
de Groot et al.

(10) Patent No.: US 7,939,277 B2
(45) Date of Patent: May 10, 2011

(54) METHODS AND ASSAYS FOR DISTINGUISHING BETWEEN DIFFERENT FORMS OF DISEASES AND DISORDERS CHARACTERIZED BY THROMBOCYTOPENIA AND/OR BY SPONTANEOUS INTERACTION BETWEEN VON WILLEBRAND FACTOR (VWF) AND PLATELETS

(75) Inventors: Philip G. de Groot, Naarden (NL); Rob Fijnheer, Bilthoven (NL); Peter J. Lenting, Amsterdam (NL); Karen Silence, Overijse (BE)

(73) Assignees: UMC Utrecht Holding BV, Utrecht (NL); Ablynx N.V., Zwijnaarde (BE)

( * ) Notice: Subject to any disclaimer, the term of this patent is extended or adjusted under 35 U.S.C. 154(b) by 613 days.

(21) Appl. No.: 11/795,162

(22) PCT Filed: Jan. 13, 2006

(86) PCT No.: PCT/EP2006/000273
§ 371 (c)(1),
(2), (4) Date: Jul. 12, 2007

(87) PCT Pub. No.: WO2006/074947
PCT Pub. Date: Jul. 20, 2006

(65) Prior Publication Data
US 2008/0096223 A1    Apr. 24, 2008

Related U.S. Application Data

(60) Provisional application No. 60/644,414, filed on Jan. 14, 2005.

(51) Int. Cl.
*G01N 31/00* (2006.01)
*G01N 33/53* (2006.01)

(52) U.S. Cl. ........ 435/7.21; 435/7.1; 436/501; 436/518; 422/50; 530/300; 530/350

(58) Field of Classification Search .................. None
See application file for complete search history.

(56) References Cited

U.S. PATENT DOCUMENTS

| | | | |
|---|---|---|---|
| 5,238,919 A | 8/1993 | Zimmerman et al. |
| 5,670,132 A | 9/1997 | Griffiths et al. |
| 5,916,805 A | 6/1999 | Nagano et al. |
| 5,976,532 A | 11/1999 | Coller et al. |
| 6,228,360 B1 | 5/2001 | Co et al. |
| 6,251,393 B1 | 6/2001 | Handin et al. |
| 6,280,731 B1 | 8/2001 | Nagano et al. |
| 6,419,934 B1 | 7/2002 | Tobinick |
| 6,517,829 B1 | 2/2003 | Frenken et al. |
| 6,759,518 B1 | 7/2004 | Kontermann et al. |
| 6,793,920 B2 | 9/2004 | Nagano et al. |
| 7,311,913 B2 | 12/2007 | Co et al. |
| 2001/0024647 A1 | 9/2001 | McLeod et al. |
| 2002/0028204 A1 | 3/2002 | Kito et al. |
| 2002/0058033 A1 | 5/2002 | Raisch et al. |
| 2003/0092892 A1 | 5/2003 | Frenken et al. |
| 2005/0136056 A1 | 6/2005 | Kageyama et al. |
| 2005/0192224 A1 | 9/2005 | Huizinga et al. |
| 2006/0149041 A1 | 7/2006 | Silence |
| 2006/0286066 A1 | 12/2006 | Basran |
| 2010/0022452 A1 | 1/2010 | Silence et al. |

FOREIGN PATENT DOCUMENTS

| | | |
|---|---|---|
| EP | 0 295 645 A2 | 12/1988 |
| EP | 0 368 684 B1 | 3/1994 |
| EP | 0 952 218 A2 | 10/1999 |
| EP | 1 002 861 A1 | 5/2000 |
| EP | 03447005.4 | 1/2003 |
| WO | WO 90/10707 A1 | 9/1990 |
| WO | WO 93/11161 A1 | 6/1993 |
| WO | WO 94/04678 A1 | 3/1994 |
| WO | WO 94/13806 A1 | 6/1994 |
| WO | WO 94/25591 A1 | 11/1994 |
| WO | WO 96/17078 A2 | 6/1996 |
| WO | WO 97/38102 A1 | 10/1997 |
| WO | WO 99/09055 A2 | 2/1999 |
| WO | WO 99/23221 A2 | 5/1999 |
| WO | WO 00/24781 A | 5/2000 |
| WO | WO 01/02853 A | 1/2001 |

(Continued)

OTHER PUBLICATIONS

Murdock, Paul J, et al.,Thrombosis and Haemostasis, vol. 78, No. 4, 1997, pp. 1272-1277.*

(Continued)

*Primary Examiner* — Lisa V Cook
(74) *Attorney, Agent, or Firm* — Wolf, Greenfield & Sacks, P.C.

(57) ABSTRACT

The invention relates to a method for distinguishing between different states or forms of diseases and disorders characterized by thrombocytopenia and/or by spontaneous interaction between Von Willebrand Factor (vWF) and platelets, and/or to predict the progression of such a disease or disorder, said method comprising the steps of providing at least one biological sample obtained from a patient suffering from, or suspected to suffer from, at least one disease or disorder characterized by thrombocytopenia and/or by spontaneous interaction between Von Willebrand Factor (vWF) and platelets and of determining the amount of activated vWF in said biological sample, in which the amount of activated vWF in the sample is representative for the different states or forms of the disease or disorder. The invention further relates to a kit-of-parts for determining the amount of activated vWF in a sample and to the use of an antibody that is capable of specifically binding activated vWF in the presence of non-activated vWF; of a part or fragment of an antibody.

24 Claims, 8 Drawing Sheets

FOREIGN PATENT DOCUMENTS

Figure 1:
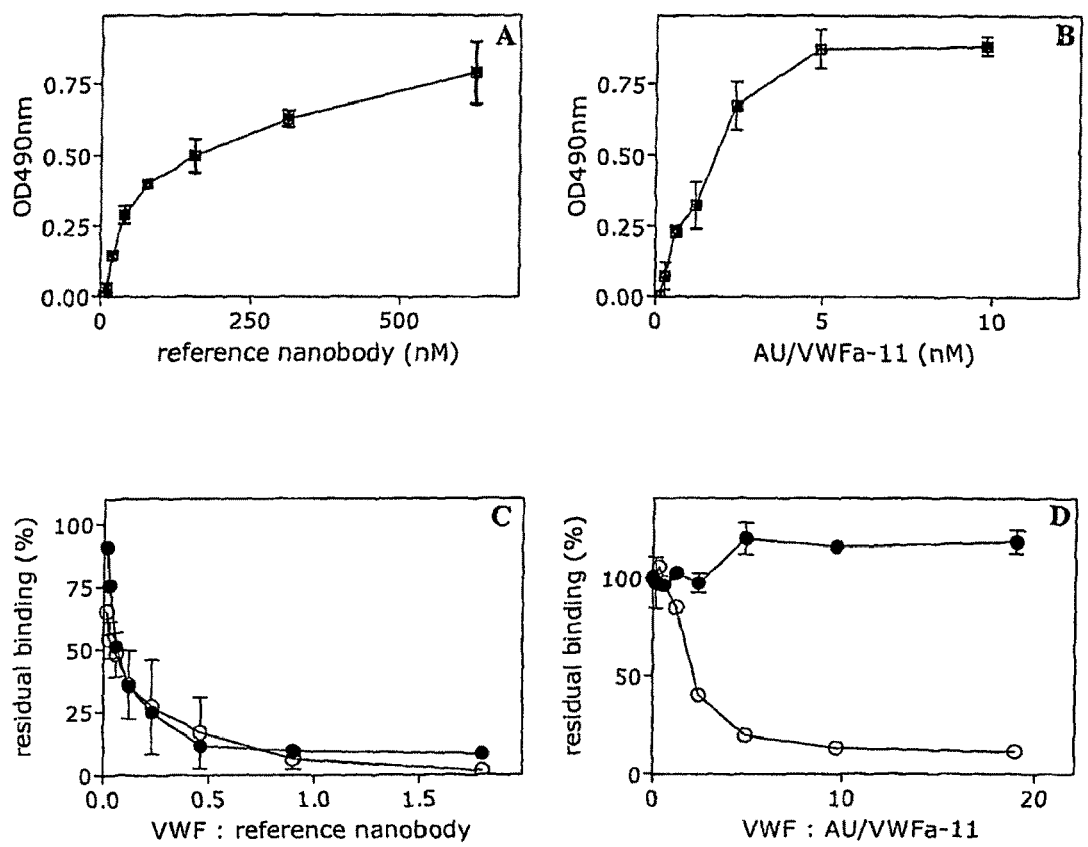

| | | |
|---|---|---|
| WO | WO 02/051351 A2 | 7/2002 |
| WO | WO 02/057445 A1 | 7/2002 |
| WO | PCT/EP03/06581 | 6/2003 |
| WO | PCT/EP03/07313 | 7/2003 |
| WO | PCT/BE03/00191 | 12/2003 |
| WO | PCT/BE03/00206 | 12/2003 |
| WO | WO 2004/003019 A2 | 1/2004 |
| WO | WO 2004/015425 A1 | 2/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2005/044858 A1 | 5/2005 |
| WO | WO 2006/074947 A2 | 7/2006 |
| WO | WO 2006/122825 A2 | 11/2006 |
| WO | WO 2008/049881 A3 | 5/2008 |

OTHER PUBLICATIONS

Paul Murdock et al. (Thromb. Haemost., vol. 78, pp. 1272-1277, 1997).*

Favaloro, E.J. et al., "Discrimination of von Willebrand's Disease (VWD) subtypes: Direct comparison of von Willebrand factor: Collagen binding assay (VWF:CBA) with monoclonal antibody (MAB) based VWF-capture systems," *Thrombosis and Haemostasis* Oct. 2000; 84(4):541-547.

Favaloro, E.J. et al., "Detection of von Willebrand disorder and identification of qualitative von Willebrand factor defects: Direct comparison of commercial ELISA-based von Willebrand factor activity options," *American Journal of Clinical Pathology* Oct. 2000; 114(4):608-618.

Favaloro, E.J. et al., "Development of a simple collagen based EILISA assay aids in the diagnosis of, and permits sensitive discrimination between Type I and Type II, von Willebrand's disease," *Blood Coagulation & Fibrinolysis* 1991; 2(2):285-291.

Lattuada, A. et al., "Mild to moderate reduction of a von Willebrand factor cleaving protease (ADAMTS-13) in pregnant women with HELLP microangiopathic syndrome," *Haematologica* Sep. 2003; 88(9):1029-1034.

Murdock, P.J. et al., "Von Willebrand factor activity detected in a monoclonal antibody-based ELISA: An alternative to the ristocetin cofactor platelet agglutination assay for diagnostic use," *Thrombosis and Haemostasis* 1997; 78(4):1272-1277.

Tsai, H.M. et al., "Antibodies to von Willebrand factor-cleaving protease in acute thrombotic thrombocytopenic purpura," *New England Journal of Medicine* Nov. 26, 1998; 339(22):1585-1594.

Veyradier, A. et al., "Laboratory diagnosis of von Willebrand disease," *International Journal of Clinical & Laboratory Research* 1998; 28(4):201-210.

Vanhoorelbeke, K. et al., "A reliable and reproducible ELISA method to measure ristocetin cofactor activity of von Willebrand factor," *Thrombosis and Haemostasis* Jan. 2000; 83(1):107-113.

[No Author Listed] The Merck Manual of Diagnosis and Therapy, 17$^{th}$ Ed. Beers et al, Editors. Merck Research Laboratories, 1999:926-7.

[No Author Listed] Von Willebrand disease. www.wikipedia.org. Accessed Dec. 30, 2008.

Arbabi Gharoudi et al., Selection and identification of single domain antibody fragments from camel heavy-chain antibodies. FEBS Lett. Sep. 15, 1997;414(3):521-6.

Berndt et al., The vascular biology of the glycoprotein Ib-IX-V complex. Thromb Haemost. Jul. 2001;86(1):178-88. Review.

Blanco et al., Formation and stability of beta-hairpin structures in polypeptides. Curr Opin Struct Biol. Feb. 1998;8(1):107-11. Review.

Bonnefoy et al., Shielding the front-strand beta 3 of the von Willebrand factor A1 domain inhibits its binding to platelet glycoprotein Ibalpha. Blood. Feb. 15, 2003;101(4):1375-83. Epub Oct. 10, 2002.

Celikel et al., von Willebrand factor conformation and adhesive function is modulated by an internalized water molecule. Nat Struct Biol. Oct. 2000;7(10):881-4.

Celikel et al., Crystal structure of the von Willebrand factor A1 domain in complex with the function blocking NMC-4 Fab. Nat Struct Biol. Mar. 1998;5(3):189-94.

Chand et al., A two-site, monoclonal antibody-based immunoassay for von Willebrand factor—demonstration that vWF function resides in a conformational epitope. Thromb Haemost. Jun. 30, 1986;55(3):318-24.

Christophe et al., A monoclonal antibody (B724) to von Willebrand factor recognizing an epitope within the A1 disulphide loop (Cys509-Cys695) discriminates between type 2A and type 2B von Willebrand disease. Br J Haematol. May 1995;90(1):195-203.

Conrath et al., Camel single-domain antibodies as modular building units in bispecific and bivalent antibody constructs. J Biol Chem. Mar. 9, 2001;276(10):7346-50. Epub Oct. 25, 2000.

Cortez-Retamozo et al., Efficient tumor targeting by single-domain antibody fragments of camels. Int J Cancer. Mar. 20, 2002;98(3):456-62.

Cruz et al., Mapping the glycoprotein Ib-binding site in the von willebrand factor A1 domain. J Biol Chem. Jun. 23, 2000;275(25):19098-105.

De Mast et al., Thrombocytopenia and release of activated von willebrand factor during early plasmodium falciparum malaria . J. Inf. Diseases 2007; 196: 622-628.

D'Haens et al., Endoscopic and histological healing with infliximab anti-tumor necrosis factor antibodies in Crohn's disease: A European multicenter trial. Gastroenterology. May 1999;116(5):1029-34.

Dong et al., Novel gain-of-function mutations of platelet glycoprotein Ibalpha by valine mutagenesis in the Cys209-Cys248 disulfide loop. Functional analysis under statis and dynamic conditions. J Biol Chem. Sep. 8, 2000;275(36):27663-70.

Dong et al., Tyrosine sulfation of glycoprotein I(b)alpha. Role of electrostatic interactions in von Willebrand factor binding. J Biol Chem. May 18, 2001;276(20):16690-4. Epub Feb. 23, 2001.

Els-Conrath et al., Camel single-domain antibodies as modular building units in bispecific and bivalent antibody constructs. J Biol Chem. Mar. 9, 2001;276(10):7346-50. Epub Oct. 25, 2000.

Emsley et al., Crystal structure of the von Willebrand Factor A1 domain and implications for the binding of platelet glycoprotein Ib. J Biol Chem. Apr. 24, 1998;273(17):10396-401.

Franchini et al., Von Willebrand factor and thrombosis. Ann Hematol. Jul. 2006;85(7):415-23. Epub Mar. 28, 2006. Review.

Fujimura et al., The interaction of botrocetin with normal or variant von Willebrand factor (types IIA and IIB) and its inhibition by monoclonal antibodies that block receptor binding. Thromb Haemost. Oct. 5, 1992;68(4):464-9.

Genbank submission; NIH/NCBI; Accession No. 1AUQ; Emsley et al; Sep. 1, 1997 (last submission).

Genbank submission; NIH/NCBI; Accession No. 1M10_A; Huizinga et al; Sep. 25, 2008 (last submission).

Genbank submission; NIH/NCBI; Accession No. AAA61295; Mancuso et al.; Jan. 14, 1995 (last submission).

Genbank submission; NIH/NCBI; Accession No. AAB34053; Clerc et al.; Jul. 27, 1995 (last submission).

Genbank submission; NIH/NCBI; Accession No. AAB39987; Schulte am Esch II et al.; Jan. 9, 1997 (last submission).

Genbank submission; NIH/NCBI; Accession No. AAB59512; Sadler; Aug. 7, 1995 (last submission).

Genbank submission; NIH/NCBI; Accession No. CAA27972; Bonthron et al.; Jan. 9, 1998 (last submission).

Genbank submission; NIH/NCBI; Accession No. NP_000164; Forestier et al; Jan. 4, 2009 (last submission).

Genbank submission; NIH/NCBI; Accession No. NP_000543; Sun et al; Jan. 4, 2009 (last submission).

Genbank submission; NIH/NCBI; Accession No. 1SQ0_A; Dumas et al.; Sep. 24, 2008 (last submission).

Goto et al., Characterization of the unique mechanism mediating the shear-dependent binding of soluble von Willebrand factor to platelets. J Biol Chem. Oct. 6, 1995;270(40):23352-61.

Groot et al., The presence of active von Willebrand factor under various pathological conditions. Curr Opin Hematol. May 2007;14(3):284-9. Review.

Holliger et al., Retargeting serum immunoglobulin with bispecific diabodies. Nat Biotechnol. Jul. 1997;15(7):632-6.

Hoogenboom et al., Mix and match: building manifold binding sites. Nat Biotechnol. Feb. 1997;15(2):125-6.
Huizinga et al., Structures of glycoprotein Ibalpha and its complex with von Willebrand factor A1 domain. Science. Aug. 16, 2002;297(5584):1176-9.
Hulstein et al., A novel nanobody that detects the gain-of-function phenotype of von Willebrand factor in ADAMTS13 deficiency and von Willebrand disease type 2B. Blood. Nov. 1, 2005;106(9):3035-42. Epub Jul. 12, 2005.
Ikeda et al., The role of von Willebrand factor and fibrinogen in platelet aggregation under varying shear stress. J Clin Invest. Apr. 1991;87(4):1234-40.
Ill et al., Design and construction of a hybrid immunoglobulin domain with properties of both heavy and light chain variable regions. Protein Eng. Aug. 1997;10(8):949-57.
Janeway et al., Ch. 3: Structure of the antibody molecule and immunogloblin genes. In Immunobiology: The immune sysyem in health and disease, 3$^{rd}$ Ed. Current Biology, Ltd, 1997;3:1-3:11.
Kageyama et al., Pharmacokinetics and pharmacodynamics of AJW200, a humanized monoclonal antibody to von Willebrand factor, in monkeys. Arterioscler Thromb Vasc Biol. Jan. 2002;22(1):187-92.
López et al., Bernard-Soulier syndrome. Blood. Jun. 15, 1998;91(12):4397-418. Review.
Mallender et al., Construction, expression, and activity of a bivalent bispecific single-chain antibody. J Biol Chem. Jan. 7, 1994;269(1):199-206.
Matsushita et al., Identification of amino acid residues essential for von Willebrand factor binding to platelet glycoprotein Ib. Charged-to-alanine scanning mutagenesis of the A1 domain of human von Willebrand factor. J Biol Chem. Jun. 2, 1995;270(22):13406-14.
Matsushita et al., Localization of von willebrand factor-binding sites for platelet glycoprotein Ib and botrocetin by charged-to-alanine scanning mutagenesis. J Biol Chem. Apr. 14, 2000;275(15):11044-9.
Miller et al., Mutation in the gene encoding the alpha chain of platelet glycoprotein Ib in platelet-type von Willebrand disease. Proc Natl Acad Sci U S A. Jun. 1, 1991;88(11):4761-5.
Muyldermans, Single domain camel antibodies: current status. J Biotechnol. Jun. 2001;74(4):277-302. Review.
Neri et al., High-affinity antigen binding by chelating recombinant antibodies (CRAbs). J Mol Biol. Feb. 24, 1995;246(3):367-73.
Nokes et al.,Von Willebrand factor has more than one binding site for platelets. Thromb Res. Jun. 1, 1984;34(5):361-6.
Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.
Rudikoff et al., Single amino acid substitution altering antigen-binding specificity. Proc Natl Acad Sci U S A. Mar. 1982;79(6):1979-83.
Ruggeri, Von Willebrand factor, platelets and endothelial cell interactions. J Thromb Haemost. Jul. 2003;1(7):1335-42. Review.
Russell et al., Pseudo-von Willebrand disease: a mutation in the platelet glycoprotein Ib alpha gene associated with a hyperactive surface receptor. Blood. Apr. 1, 1993;81(7):1787-91.
Sadler et al., Molecular mechanism and classification of von Willebrand disease. Thromb Haemost. Jul. 1995;74(1):161-6. Review.

Sadler, Biochemistry and genetics of von Willebrand factor. Annu Rev Biochem. 1998;67:395-424. Review.
Savage et al., Initiation of platelet adhesion by arrest onto fibrinogen or translocation on von Willebrand factor. Cell. Jan. 26, 1996;84(2):289-97.
Silence et al., ALX-0081 Nanobody#, an Engineered Bivalent Anti-Thrombotic Drug Candidate with Improved Efficacy and Safety as Compared to the Marketed Drugs. Blood. ASH Annual Meeting Abstracts. Nov. 1, 2006; 108(11): Abstract 896.
Tait et al., Phenotype changes resulting in high-affinity binding of von Willebrand factor to recombinant glycoprotein Ib-IX: analysis of the platelet-type von Willebrand disease mutations. Blood. Sep. 15, 2001;98(6):1812-8.
Tanha et al., Selection by phage display of llama conventional V(H) fragments with heavy chain antibody V(H)H properties. J Immunol Methods. May 1, 2002;263(1-2):97-109.
Thompson et al., Advances in the pathogenesis and treatment of acute coronary syndromes. J La State Med Soc. May 1999;151(5):272-7. Review. Abstract only.
Triplett, Coagulation and bleeding disorders: review and update. Clin Chem. Aug. 2000;46(8 Pt 2):1260-9. Review.
Valle et al., Infliximab. Expert Opin Pharmacother. Jun. 2001;2(6):1015-25. Review.
Vasudevan et al., Modeling and functional analysis of the interaction between von Willebrand factor A 1 domain and glycoprotein Ibalpha. J Biol Chem. Apr. 28, 2000;275(17):12763-8.
AAP82060 standard protein 20 AA (sequence from EP 0 295 645).
AAR40233 standard protein 15 AA (sequence from US 5,238,919).
Deffar et al., Nanobodies—the new concept in antibody engineering. Afr J Biotechnol. Jun. 17, 2009;8(12):2645-52.
Groot et al., The active conformation of von Willebrand factor in patients with thrombotic thrombocytopenic purpura in remission. J Thromb Haemost. Jun. 2009;7(6):962-9.
Wu et al , Inhibition of the von Willebrand (VWF)-collagen interaction by an antihuman VWF monoclonal antibody results in abolition of in vivo arterial platelet thrombus formation in baboons. Blood. May 15, 2002;99(10):3623-8.
Vincke et al. General Strategy to humanize a camelid single-domain antibody and identification of a universal humanized nanobody scaffold. J Biol Chem 284: 3273-3284.
[No Author Listed] embolism. www.wikipedia.org. Accessed Apr. 19, 2010. 4 pages.
[No Author Listed] Immunochemistry. Nankodo Co., Ltd., Jul. 15, 1983 (1st ed.), pp. 35-36.
[No Author Listed] The Merck Manual of Diagnosis and Therapy, 17th Ed. Beers et al, Editors. Merck Research Laboratories, 1999:2057-8.
Badreldin et al., Gaseous emboli during off-pump surgery with T-graft technique, two different mechanisms. Interact Cardiovasc Thorac Surg. May 2010;10(5):766-9. Epub Feb. 12, 2010.
Varga-Szabo et al., Cell adhesion mechanisms in platelets. Arterioscler Thromb Vasc Biol. Mar. 2008;28(3):403-12. Epub Jan. 3, 2008.
Ohno et al., Antigen-binding specificities of antibodies are primarily determined by seven residues of VH. Proc Natl Acad Sci U S A. May 1985;82(9):2945-9.

* cited by examiner

METHODS AND ASSAYS FOR DISTINGUISHING BETWEEN DIFFERENT FORMS OF DISEASES AND DISORDERS CHARACTERIZED BY THROMBOCYTOPENIA AND/OR BY SPONTANEOUS INTERACTION BETWEEN VON WILLEBRAND FACTOR (VWF) AND PLATELETS

RELATED APPLICATIONS

This application is a national stage filing under 35 U.S.C. §371 of international application PCT/EP2006/000273, filed Jan. 13, 2006 and claims the benefit under 35 U.S.C. §119(e) of U.S. provisional application Ser. No. 60/644,414, filed Jan. 14, 2005.

The present invention relates to methods for distinguishing between different states or forms of diseases and disorders characterized by thrombocytopenia and/or by spontaneous interaction between Von Willebrand Factor (vWF) and platelets, and/or to predict the progression of such a disease or disorder.

In particular, the present invention relates to methods for providing parameters that can be used to distinguish between different states or forms of diseases and disorders characterized by thrombocytopenia and/or by spontaneous interaction between Von Willebrand Factor (vWF) and platelets; to follow the progression of such a disease or disorder; to make predictions about the progression of such a disease or disorder; to determine a suitable treatment or treatment regimen for such a disease or disorder; to determine the therapeutic efficacy of such a treatment; and/or where indicated to modify such a treatment.

Further aspects, embodiments, uses, applications and advantages of the invention will become clear from the further description hereinbelow.

The invention is based on the surprising finding that the levels of activated vWF in a biological sample obtained from a patient suffering from, or suspected to suffer from, at least one disease or disorder characterized by thrombocytopenia and/or by spontaneous interaction between Von Willebrand Factor (vWF) and platelets can be used to distinguish between different states or forms of diseases and disorders characterized by thrombocytopenia and/or by spontaneous interaction between Von Willebrand Factor (vWF) and platelets; to follow the progression of such a disease or disorder; to make predictions about the progression of such a disease or disorder; to determine a suitable treatment for such a disease or disorder; to determine the therapeutic efficacy of such a treatment; and/or where indicated to modify such a treatment.

Thus, in a first aspect, the invention relates to a method for distinguishing between different states or forms of diseases and disorders characterized by thrombocytopenia and/or by spontaneous interaction between Von Willebrand Factor (vWF) and platelets, and/or to predict the progression of such a disease or disorder, said method comprising the steps of:
a) providing at least one biological sample obtained from a patient suffering from, or suspected to suffer from, at least one disease or disorder characterized by thrombocytopenia and/or by spontaneous interaction between Von Willebrand Factor (vWF) and platelets;
b) determining the amount of activated vWF in said biological sample;
in which the amount of activated vWF in the sample is representative for the different states or forms of the disease or disorder.

The biological sample used in the method of the invention is preferably a sample that contains vWF, more preferably a sample that contains vWF and platelets. In particular, the biological sample may be chosen from whole blood, plasma, serum or other suitable blood fractions.

In the method of the invention, the amount (e.g. the absolute amount, level and/or concentration) of activated vWF in the sample may be compared to a reference value for the amount of activated vWF, for example to a reference value obtained from a patient or group of patients without the disease or disorder; to a reference value obtained from a patient or group of patients with the disease or disorder; to a reference value obtained from a patient or group of patients with a different form of the disease or disorder. The amount of activated vWF in the sample may also be compared to the amount of vWF in one or more further samples obtained from the same patient (e.g. obtained at earlier and/or later points in time). Reference is made to the Experimental Section below.

The amount of activated vWF may also be compared to another suitable parameter of the sample.

For example, the amount of activated vWF in the sample also may be compared to the amount of non-activated vWF and/or to the total amount of (activated and non-activated) vWF in the same sample. Also, a suitable ratio of the amount of activated vWF and non-activated vWF in the sample (such as the percentage activated vWF in the sample relative to the total amount of vWF in the sample) may be compared to a reference value, for example to a reference value obtained from a patient or group of patients without the disease or disorder and/or to a reference value obtained from a patient or group of patients with the disease or disorder. For this purpose, the amount of non-activated vWF and/or the total amount of vWF may be determined in a manner known per se. Reference is again made to the Experimental Section below.

When the sample used contains both vWF and platelets, the amount of activated vWF in the sample also may be compared to the platelet number in the same sample. Also, a suitable ratio of the amount of activated vWF in the sample and the platelet number in the sample may be compared to a reference value, for example to a reference value obtained from a patient or group of patients without the disease or disorder and/or to a reference value obtained from a patient or group of patients with the disease or disorder. For this purpose, the platelet number of the sample may be determined in a manner known per se. Reference is again made to the Experimental Section below.

The method according to the invention can in particular be used to (provide one or more parameters that can be used by the clinician to) distinguish between different states or forms of, to follow the progression of, to make predictions about the progression of; to determine a suitable treatment or treatment regimen for; to determine the therapeutic efficacy of a treatment for; and/or where indicated to modify a treatment for, the following diseases and disorders: Thrombocytopenic Purpura (TTP), pre-eclampsia, HELLP syndrome, Von Willebrand disease Type 2; DIC (diffuse intracellular coagulation) or Sepsis; malignant hypertension; antiphospholipid syndrome; exposure to carcinogens in general; after platelet transfusion with platelet concentrates (for perfusion); malaria; venous and/or arterial thrombosis and bone-marrow transplantation.

According to one preferred, but non-limiting embodiment, the method according to the invention is used to distinguish between different states or forms of, to follow the progression of, to make predictions about the progression of; to determine a suitable treatment or treatment regimen for; to determine the therapeutic efficacy of a treatment for; and/or where indicated to modify a treatment for, Thrombocytopenic Purpura (TTP). In particular, according to this embodiment, the method of the invention can be used to distinguish between patients with acquired TTP and patients with congenital TTP. As described in the Experimental Part below, a sample obtained from a patient with the congenital form of TTP will contain significantly more activated vWF than a sample obtained from a patient with the acquired form of TTP, thus allowing patients with the congenital form of TTP to be distinguished from patients with the acquired form of TTP (e.g. by the clinician).

According to another preferred, but non-limiting embodiment, the method according to the invention is used to distinguish between different states or forms of, to follow the progression of, to make predictions about the progression of; to determine a suitable treatment or treatment regimen for; to determine the therapeutic efficacy of a treatment for; and/or where indicated to modify a treatment for, pre-eclampsia and/or HELLP syndrome. For example, according to this embodiment, the method of the invention can be used to distinguish between patients with pre-eclampsia and patients with HELLP syndrome (a severe form of pre-eclampsia). This embodiment may also be used to follow and/or predict the progress of pre-eclampsia, and in particular to predict which patients with pre-eclampsia will develop HELLP and/ or determine which patients with pre-eclampsia are at an increased risk of developing HELLP. As described in the Experimental Part below, a sample obtained from a patient with HELLP will contain significantly more activated vWF than a sample obtained from either a healthy pregnant subject and than a sample obtained from a patient with pre-eclampsia, thus allowing patients with the HELLP syndrome to be distinguished from healthy subjects and from patients with the pre-eclampsia (e.g. by the clinician), and also to follow and/or predict the progress of pre-eclampsia, and in particular to predict which patients with pre-eclampsia will develop HELLP and/or determine which patients with pre-eclampsia are at an increased risk of developing HELLP.

Generally, in the invention, a sample can be considered to contain an "increased" or "elevated" level of activated vWF if the amount, level or concentration of activated vWF in said sample is more then the following value:

[Average]+[2×SD], in which

[Average]=the average amount of activated vWF in samples obtained from a group of healthy volunteers;
[2×SD]=standard deviation for the samples;

it being understood that in practice, samples from non-healthy patients may contain levels of activated vWF that are significantly higher than this (compared the values described in the Experimental Part below).

In the method according to the invention, the amount of activated vWF may be determined in any manner known per se, for example using suitable spectrophotometric techniques, chromatographic techniques, mass spectrometry techniques or other suitable techniques known per se.

Preferably, however, the amount of activated vWF is determined by contacting the biological sample with a binding agent that is capable of specifically binding activated vWF in the presence of non-activated vWF, and then optionally determining the amount of activated vWF bound to the binding agent.

This can for example be performed using any suitable binding assay involving the binding agent, as will be clear to the skilled person, for example an immunosorbent assay, such as ELISA or RIA; assays involving the use of microarrays; affinity techniques involving columns, beads or other supports to which the binding agent attached (covalently or otherwise); use of cell-sorting techniques (such as FACS) involving the use of binding agents attached (covalently or otherwise) to beads or to a suitable label or marker (e.g. a fluorescent marker); and other techniques involving the use of suitably labelled binders.

It is also envisaged to perform the method of the invention through the use of a suitable carrier (such as a strip of paper, a tube, a well, or another suitable surface or medium) to which the binding agent is attached (covalently or otherwise). This carrier can then be exposed to the sample, in suitable manner and for a suitable period of time, after which the amount of activated vWF bound to the carrier is determined. This may for example be performed through a subsequent step of eluting the bound vWF from the carrier and then determining the amount of eluted activated vWF; by comparing the amount of remaining free binding sites on the carrier before and after exposure to the sample; and/or through directly measuring the amount of activated vWF bound to the carrier. For example, it is envisaged that the carrier may be provided with indicator means that indicate the amount of vWF bound to the carrier (e.g. through a change in colour); or that the carrier can be suitably developed to provide a signal (e.g. change of colour) that is a measure for the amount of activated vWF bound to the carrier.

Methods, techniques and equipment for performing such binding assays will also be clear to the skilled person; reference is for example made to the Experimental Part below. For the binding assay, the binding agent may also be immobilized on a suitable support, as will be again clear to the skilled person.

Any suitable binding agent that can specifically bind activated vWF in the presence of non-activated vWF (i.e. a binding agent that can distinguish between the activated/binding conformation of vWF and the non-activated/non-binding conformation of vWF) can be used.

For example, the binding agent can be a protein or polypeptide that is capable of specifically binding activated vWF in the presence of non-activated vWF, such as an antibody that is capable of specifically binding activated vWF in the presence of non-activated vWF; a part of fragment of an antibody, in which said part or fragment is capable of specifically binding activated vWF in the presence of non-activated vWF; or a protein or polypeptide that contains and/or comprises one or more parts of fragments of an antibody, in which at least one of said parts or fragments is capable of specifically binding activated vWF in the presence of non-activated vWF.

In particular, said part or fragment may be a variable domain, such as a heavy chain variable domain and/or a light chain variable domain, or a ScFv comprising both a heavy chain variable domain and/or a light chain variable domain. Such antibodies and fragments, and methods for obtaining the same, will be clear to the skilled person; reference is for example made to Roitt et al., "*Immunology*" (6th. Ed.), Mosby/Elsevier, Edinburgh (2001); and Janeway et al., "*Immunobiology*" (6th Ed.), Garland Science Publishing/ Churchill Livingstone, New York (2005).

According to one preferred, but non-limiting embodiment, the binding agent can be a so-called "heavy chain antibody" that is capable of specifically binding activated vWF in the presence of non-activated vWF; a part of fragment of a heavy chain antibody, in which said part or fragment is capable of specifically binding activated vWF in the presence of non-activated vWF; or a protein or polypeptide that contains and/ or comprises one or more parts of fragments of a heavy chain antibody, in which at least one of said parts or fragments is capable of specifically binding activated vWF in the presence of non-activated vWF (for example, a multivalent protein containing two or more such fragments. Such a multivalent protein may have a higher affinity and/or specificity for the activated form of vWF—i.e. compared to the corresponding monovalent form—and thus may lead to an assay with improved sensitivity; less background and/or a better signal-to-noise ratio).

Heavy chain antibodies and methods for obtaining the same have been described in the art, see for example the following references, that are cited as general background art: WO 94/04678 (=EP 656 946), WO 96/34103 (=EP 0 822 985) and WO 97/49805 by Vrije Universiteit Brussel; WO 97/49805 by Vlaams Interuniversitair Instituut voor Biotechnologie; WO 94/25591 (=EP 0 698 097) and WO 00/43507 by Unilever N.V.; WO 01/90190 by the National Research Council of Canada; WO 03/025020 (=EP 1 433 793) by the Institute of Antibodies; WO 04/062551, WO 04/041863, WO 04/041865, WO 04/041862 by applicant; as well as for example Hamers-Casterman et al., Nature, Vol. 363, p. 446 (1993) and Riechmann and Muyldermans, Journal of Immunological Methods, 231 (1999), p. 25-38.

For example, heavy chain antibodies against a desired antigen can be obtained from a species of Camelid immunized with said antigen, as described in the general prior art mentioned above.

As also mentioned in the above references, naturally occurring heavy chain antibodies do not contain the light chains present in naturally occurring conventional 4-chain antibodies (that natively contain both heavy chains and light chains). Because of this, such naturally occurring heavy chain antibodies have also been referred to in the art as "single chain antibodies" (see for example WO 02/085945; and not to be confused with so-called "single chain Fv's" or "scFv's", which are synthetic polypeptides comprising a $V_H$ domain covalently linked to a $V_L$ domain) and as "immunoglobulins devoid of light chains" (see for example EP 0 656 946 and some of the further general background art mentioned above), which terms for the purposes of the present description should be considered equivalent to the term "heavy chain antibody" as used herein.

As also mentioned in these references, the heavy chains of naturally occurring heavy chain antibodies contain CH3 domains, CH2 domains and a variable domain, but—in addition to the light chains—lack the CH1 domains present in the heavy chains of naturally occurring conventional 4-chain antibodies. Herein, the variable domains from naturally occurring heavy chain antibodies will also be referred to as "$V_{HH}$ domains", in order to distinguish said variable domains from the variable domains from conventional 4-chain antibodies, which are commonly referred to as "$V_H$ domains".

Generally, $V_{HH}$ domains have a structure that retains the immunoglobulin fold of conventional $V_H$ domains. However, compared to $V_H$ domains, $V_{HH}$ domains contain one or more substitutions in their amino acid sequence (and in particular in their framework regions) that make the region(s)/residues of the $V_{HH}$ domain that in a $V_H$ domain would form the $V_H/V_L$ interphase more hydrophobic (see the general background art cited above).

Also, as mentioned in the general background art cited above, heavy chain antibodies and $V_{HH}$ domains have the major advantage that they are capable of binding an antigen without the presence of any light chains or light chain variable domains, respectively. This makes heavy chain antibodies and $V_{HH}$ domains easier to obtain, to develop, to prepare (in particular) on a large scale, to use and/or to bind to a support than conventional 4-chain antibodies or light chain or heavy chain variable domains thereof. For example, the immobilization of $V_{HH}$ domains on a solid support has been described in the International application WO 01/40310 by Hindustan Lever Limited.

According to a particularly preferred embodiment, the binding agent is a NANOBODY®, for which term reference is made to the prior art mentioned above, to the non-prepublished International application PCT/EP2005/011819 by applicant (filed on Nov. 4, 2005 and entitled "*Method for generating variable domain sequences of heavy chain antibodies*") and to the further published and unpublished patent applications of Ablynx N.V. [Note: NANOCLONE®, NANOBODY® and NANOBODIES® are subject to trademark protection or applications therefor by Ablynx N.V.]. Generally, NANOBODIES® can be described as proteins that have some of the functional properties and structural features that are characteristic of naturally occurring $V_{HH}$ domains. A NANOBODY® may for example be a naturally occurring $V_{HH}$ domain, a "humanized" $V_{HH}$ domains or a "camelized" $V_H$ domains, as well as a partially or fully synthetic protein, as long as the foregoing have (at least some of) the functional properties and structural features that are characteristic of naturally occurring $V_{HH}$ domains. Reference is also made to the non-prepublished U.S. provisional application 60/683,474 by applicant (referred to below), which describes various NANOBODIES® against vWF (including NANOBODIES® against activated vWF). As also mentioned in these applications by applicant and in the other prior art mentioned above, NANOBODIES® can also be formatted and used in multivalent and/or multispecific formats.

The International application WO 04/062551 by applicant, incorporated herein by reference, describes heavy chain antibodies against different domains of vWF and against both the activated and non-activated forms of vWF, the VHH domains of such heavy chain antibodies, NANOBODIES® based thereon, and methods for obtaining the same. These heavy chain antibodies and VHH domains are particularly suited for use in the methods described herein. For example, a heavy chain antibody according to WO 04/062551 (or a $V_{HH}$ domain thereof) that is directed against the activated form of vWF (e.g. against the activated form of the A1 domain of vWF) can be used to determine the amount of activated vWF in a sample in accordance with the method of the invention, whereas a heavy chain antibody according to WO 04/062551 (or a $V_{HH}$ domain thereof or a NANOBODY® based thereon) that is directed against the non-activated form of vWF (e.g. against the non-activated form of the A1 domain) or against both the activated and non-activated form of vWF (e.g. against the A3 domain of vWF) can be used in the method of the invention to determine the amount of non-activated vWF in a sample or the total amount of vWF in a sample, respectively.

Some particularly preferred, but non-limiting NANOBODIES® directed against the activated form of vWF are the NANOBODIES® directed against the activated form of the A1 domain of vWF that are described in the International application WO 04/062551, including but not limited to AU/VWFa-11 ("a-11"); AU/VWFa-12 ("a-12") and/or AU/VWFa-16 ("a-16"). As mentioned above, it envisaged that the use of multivalent (such as bivalent or trivalent) forms of these NANOBODIES® (i.e. polypeptides in which two, three or more of these NANOBODIES® (which may be the same or different) are linked to each other, optionally via a suitable linker sequence, again as described in International application WO04/062551) may lead to higher affinity and/or specificity for the activated form of vWF—i.e. compared to the corresponding monovalent NANOBODY®—and thus may lead to an assay with improved sensitivity; less background and/or a better signal-to-noise ratio. For the design and the preparation of such multivalent proteins, reference is again made to WO 04/062551, as well as to the general background art on NANOBODIES® referred to above.

Other NANOBODIES® that can be used in the methods of the present invention are described in the non-prepublished U.S. provisional application 60/683,474 by applicant (filed on May 20, 2005 and entitled "*NANOBODIES® for the treatment of aggregation-mediated disorders*").

As already mentioned hereinabove, and as will be further explained in the Experimental Part below, the values determined using the methods of the invention can be used (e.g. by the clinician) as parameters in order to distinguish between different states or forms of diseases and disorders characterized by thrombocytopenia and/or by spontaneous interaction between Von Willebrand Factor (vWF) and platelets; to follow the progression of such a disease or disorder; to make predictions about the progression of such a disease or disorder; to determine a suitable treatment for such a disease or disorder; to determine the therapeutic efficacy of such a treatment; and/or where indicated to modify such a treatment. This will be within the skill of the clinician, on the basis of the disclosure herein.

The methods and assays of the invention can also be used in research, for example into the diseases and/or disorders mentioned above and/or into the role of vWF in such diseases or disorders.

In a further aspect, the invention relates to a kit-of-parts for determining the amount of activated vWF in a sample, and in particular for use in a method as described herein, said kit-of-parts comprising at least a binding agent that is capable of specifically binding activated vWF in the presence of non-activated vWF (optionally attached to a suitable carrier or surface, as described hereinabove); and optionally comprising means for determining the total amount of (activated and non-activated) vWF in the sample (as will be clear to the skilled person); and/or means for determining the platelet number in the sample (as will be clear to the skilled person); and/or instructions for use; and/or one or more parts, elements or components of kits for binding assays known per se (as will be clear to the skilled person); wherein said kit-of-parts is optionally packaged in a suitable packaging or container. In said kit-of-parts, the binding agent is preferably as further described above.

The invention also relates to the use of a binding agent that is capable of specifically binding activated vWF in the presence of non-activated vWF, for distinguishing between different states or forms of diseases and disorders characterized by thrombocytopenia and/or by spontaneous interaction between Von Willebrand Factor (vWF) and platelets, and/or to predict the progression of such a disease or disorder; and/or in the methods described hereinabove, and/or in a kit-of-parts as described hereinabove.

Said binding agent is preferably as further described hereinabove, and may for example be an antibody or a part or fragment of an antibody (wherein said antibody, part or fragment is capable of specifically binding activated vWF in the presence of non-activated vWF); a protein or polypeptide containing and/or comprising at least one part or fragment of such an antibody; a heavy chain antibody or a part or fragment thereof (wherein said heavy chain antibody, part or fragment is capable of specifically binding activated vWF in the presence of non-activated vWF); a protein or polypeptide containing and/or comprising at least one part or fragment of such a heavy chain antibody; a NANOBODY® (wherein said NANOBODY® is capable of specifically binding activated vWF in the presence of non-activated vWF); or a protein or polypeptide containing one or more NANOBODIES®.

The invention also relates to the use of a binding agent (as described above) that is capable of specifically binding activated vWF in the presence of non-activated vWF; for preventing or treating diseases and disorders characterized by thrombocytopenia and/or by spontaneous interaction between Von Willebrand Factor (vWF) and platelets, or for slowing or preventing the (further) progression thereof.

Also, for this purpose, said binding agent may be incorporated into a suitable pharmaceutical form or formulation using one or more pharmaceutically acceptable carriers, diluents or excipients, in a manner known per se, and administered in therapeutically effective amounts to a subject in need of such prevention or treatment, according to a suitable treatment regimen and via a suitable route of administration. Reference is again made to for example WO 04/062551 and to U.S. provisional application 60/683,474, incorporated herein by reference.

The invention also relates to the use of a binding agent (as defined above) that is capable of specifically binding activated vWF in the presence of non-activated vWF, for selectively removing activated vWF from a sample or fluid, and in particular from a sample or fluid that contains both activated vWF as well as non-activated vWF. The sample may in particular be a biological sample as described above, for example a biological sample obtained from a patient. The fluid may for example be a biological fluid such as blood or plasma, also for example obtained from a patient.

As a non-limiting example of a method according to the latter embodiment, blood may be taken from a patient (either batch-wise or essentially continuously), after which activated vWF is selectively removed from the blood using the binding agent/method of the invention, after which the blood (with a decreased amount of activated vWF) is returned to the patient. For this purpose, the binding agent may be bound to a carrier, in order to facilitate the separation from the binding agent with the activated vWF from the blood to be returned to the patient. Suitable carriers and separation techniques (such as the use of specifically adapted dialysis equipment) will be clear to the skilled person, and are for example described in WO 04/062551 and in the U.S. provisional application 60/683,474. Alternatively, the binding agent may be tagged with a tag that facilitates removal of the tagged binding agent (with the activated vWF bound thereto) from the circulation. Such a tagged binding agent may then be administered to a patient (in any suitable manner known per se, for example by introduction directly into the circulation using intravenous injection or infusion) in an amount that is suitable for removing the desired amount of activated vWF from the circulation from the patient. Suitable tags for use in this embodiment (such as galactose), methods for attaching the same to the binding agent, and methods for performing this embodiment (such as the amounts to be administered) will be clear to the skilled person. For example, but without limitation, the methods of this embodiment may be used in the (selective) removal of activated vWF for or as part of the treatment of TTP, HELLP, type 2B vWF or other thrombotic disorders (including but not limited to those mentioned herein).

Various agents that block platelet thrombus formation are currently examined for their anti-thrombotic use to prevent ischemic complications. Although some agents have reached the clinic, the search for the "ideal anti-thrombotic drug" is still in process. NANOBODIES®, such as AU/VWFa-11 mentioned in the examples below, can be used as a treatment option to prevent thrombotic complications caused by the presence of circulating active VWF. Since AU/VWFa-11 recognizes active but not latent VWF, this NANOBODY® therefore removes only the dangerous vWF molecules. In contrast, levels of normal VWF remain unaffected, thereby avoiding the risk of bleeding complications as a result from VWF that are too low. Clearance of the vWF-nanobody complex may be accelerated by modifications of the NANOBODY®. Such modifications include but are not limited to for instance galactose to enhance recognition by galactose-recognizing scavenger-receptors (asialoglycoprotein-receptor). Also other tags can be attached covalently to AU/VWFa-11.

As already mentioned in the applications by applicant referred to above, NANOBODIES® may also be used with advantage for imaging purposes. According to the present invention, it has been found that binding agents that are capable of specifically binding activated vWF in the presence of non-activated vWF, and in particular NANOBODIES® that are capable of specifically binding activated vWF in the presence of non-activated vWF, can in particular be used for in vivo imaging in order to localize platelet-rich thrombi. For this purpose, a binding agent may be used that is labelled in any suitable manner (for example, as described for NANOBODIES® in the U.S. provisional application 60/683,474). The labelled binding agent may then be administered to a subject (in any suitable manner known per se, for example by introduction directly into the circulation using intravenous injection or infusion) in an amount that is suitable for visualizing any platelet-rich thrombi that may be present in the circulation of the subject, after which the thrombi can be visualized in any manner known per se, for example using NMR, MRI, PET or any other suitable non-evasive technique (depending on the label used).

For example, NANOBODY® AU/VWFa-11 described below can be used as a tracer-agent to localize thrombi in the vasculature of patients. In contrast to VWF that is circulating in plasma, the VWF that is present in thrombi is present in an active, platelet-binding conformation. Because NANOBODY® AU/VWFa-11 selectively recognizes active-VWF, this NANOBODY® will be selectively targeted to VWF present in thrombi. When the NANOBODY® is appropriately labelled, it therefore specifically localizes the thrombus. Appropriate labelling includes but is not limited to radionuclides used in nuclear medicine (such as $^{111}$In, $^{67}$Ga, $^{68}$Ga, $^{99m}$Tc), labels used for magnetic resonance imaging (such as Gd) or markers for detection via optical techniques (such as colloidal gold).

The method of the invention can also be used to determine whether there are conditions of high or increased shear rate at any point or location within the circulation of a subject. According to the present invention, it has been found that the presence of such conditions of high or increased shear rate in the circulation leads to an increase of the levels of activated vWF in blood. The methods and binding agents described herein, which allow selective measurement of the levels of activated vWF in blood, serum or another biological sample, even in the presence of non-activated vWF, can therefore be used to determine whether there are increased levels of activated vWF—i.e. compared to a baseline level and/or by measuring the ratio of the level of activated vWF and the total level of vWF (or the level of non-activated vWF—in the blood or in a blood sample obtained from a patient, which may alert the clinical to the fact that conditions of high or increased shear rate are present somewhere in the circulation of a patient. This may for example, without limitation, be an indication of the presence of a full or partial constriction of the blood flow somewhere in the body of the patient, for example due to the presence of a thrombus or of atherosclerotic plaques in one or more of the blood vessels (veins and/or arteries) of the subject. These and other examples of diseases, conditions and disorders that are associated with and/or that may lead to constriction of blood flow and/or to conditions of high shear rate in the circulation of a patient will be clear to the skilled person, and the methods and binding agents described herein may be used for the (early) detection and/or diagnosis of all such diseases, conditions and disorders.

The invention will now be further described by means of the non-limiting Experimental Part below and the attached non-limiting Figures, in which:

FIG. 1 is a graph showing differential binding of reference NANOBODY® and AU/VWFa-11 to wt-VWF and ristocetin-activated VWF. FIG. 1A/FIG. 1B: Pd-VWF was immobilized in microtiter wells (1 µg/ml, overnight at 4° C.) and incubated with different concentrations biotinylated reference NANOBODY® (FIG. 1A, 0-625 nM) and AU/VWFa-11 (FIG. 1B, 0-10 nM). Bound antibody was detected with HRP-conjugated streptavidin. FIG. 1C/FIG. 1D: Pd-VWF coated microtiter wells were incubated with reference NANOBODY® (62.5 nM, FIG. 1C) and AU/VWFa-11 (1.9 nM, FIG. 1D) in the presence or absence of different concentrations of wt-VWF (●), or VWF preincubated with 1 mg/ml ristocetin (5 min, room temperature, ○)(0-90 nM for the reference NANOBODY® and 0-20 nM for AU/VWFa-11). Bound antibody was monitored using streptavidin-HRP. Binding in the absence of VWF was set to be 100%. Residual binding in the presence of VWF was plotted against the ratio VWF (nM): antibody (nM). Data represent the mean±SD of 3 experiments.

Figure 2:
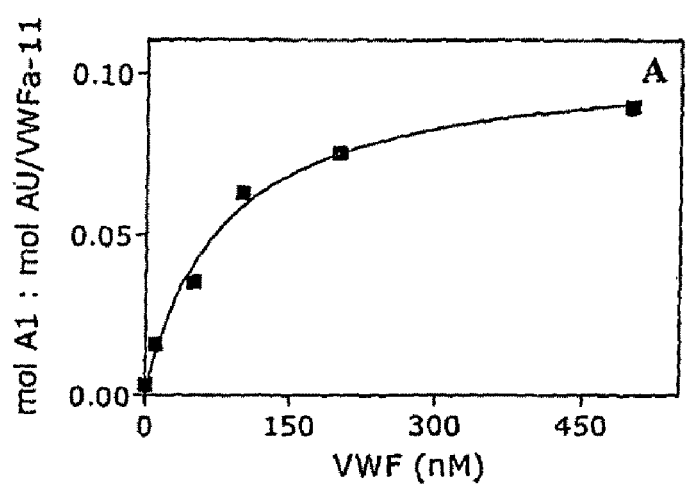
Figure 2:
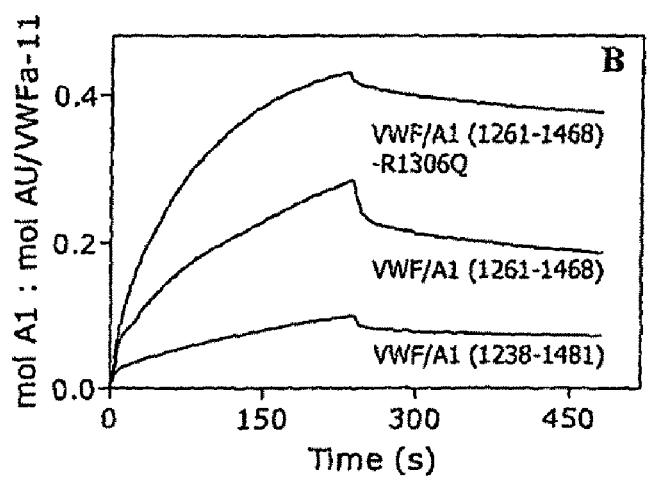

FIG. 2 is a graph showing the characteristics of the interaction between AU/VWFa-11 and the A1 domain. FIG. 2A: Different concentrations of the A1 domain (0-500 nM) were perfused over a Biacore® CM5-sensor chip coated with 0.08 pmol/mm$^2$ AU/VWFa-11 at a flowrate of 20 µl/min. The response at equilibrium (mol A1: mol AU/VWFa-11) was plotted against the concentration of VWF/A1 that was perfused over the chip. FIG. 2B: VWF/A1(1238-1481), VWF/A1(1261-1468) and VWF/A1(1261-1468)/R1306Q (500 nM) were perfused over a Biacore® CM5-sensor chip coated with 0.12 pmol/mm$^2$ AU/VWFa-11 at a flowrate of 5 µl/min. Binding was allowed for 240 s, then buffer was perfused over the chip to allow dissociation.

Figure 3:
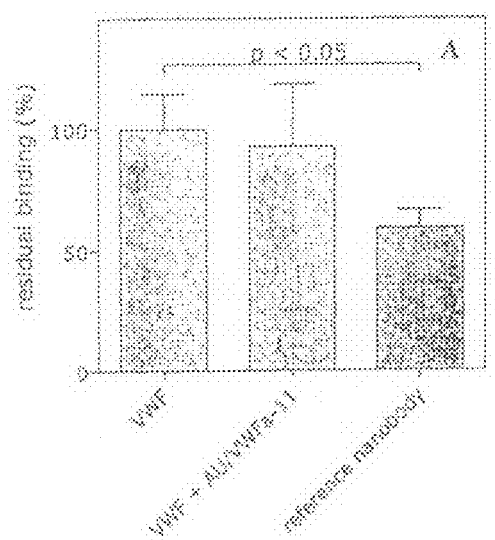
Figure 3:
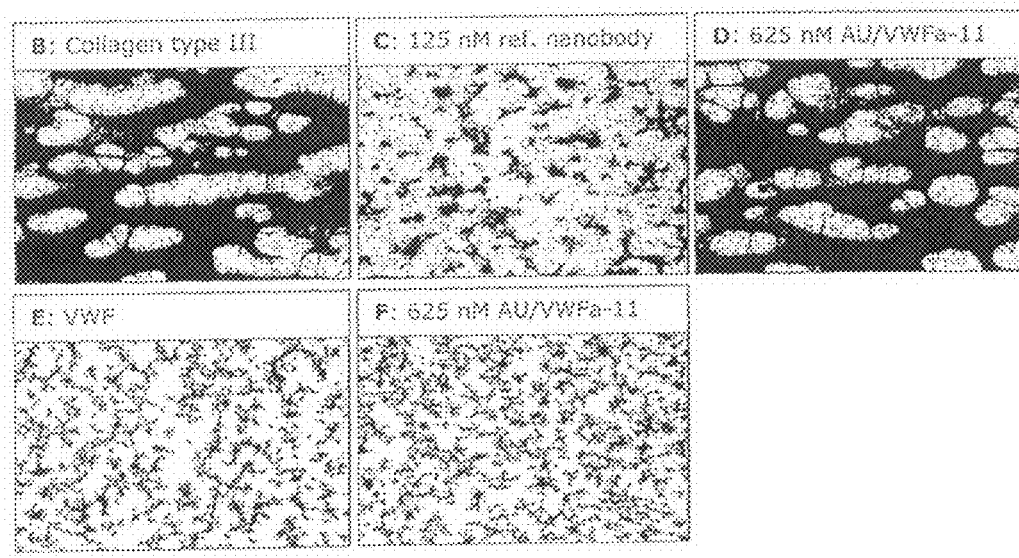
Figure 3:
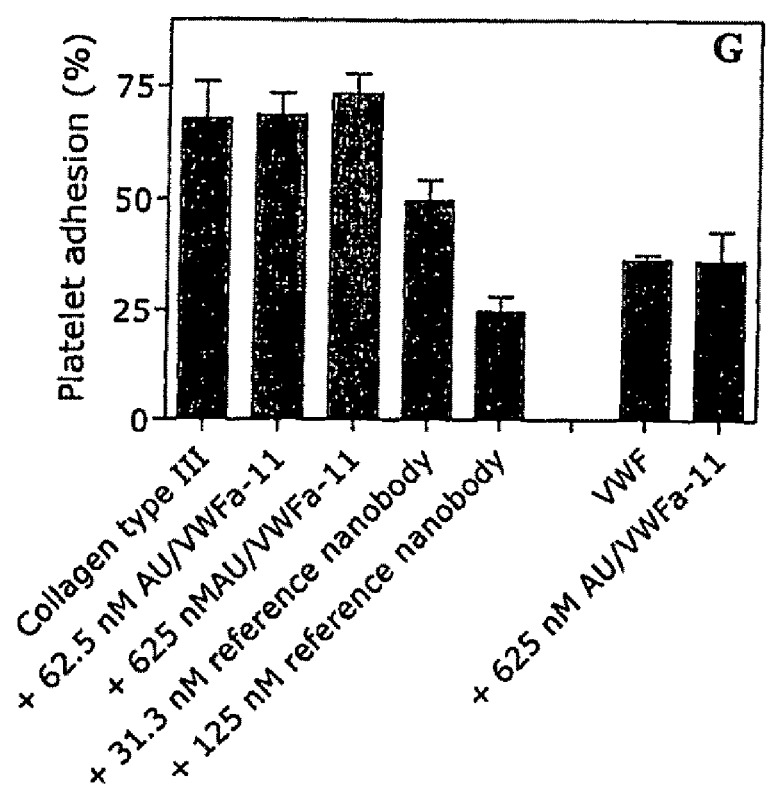

FIG. 3 is a graph showing different binding sites for GpIbα and AU/VWFa-11. FIG. 3A: Microtiter wells were coated with wt-VWF (37 nM in 50 mM NaHCO$_3$ buffer), overnight at 4° C. After blocking wells 1 h at room temperature with 0.5% PVP in PBS, wells were incubated with AU/VWFa-11 or reference NANOBODY® (1.25 µM in PBS, 1 h, room temperature). After washing with PBS, CHO-cells expressing the GpIb-IX-V complex (1×10$^5$ cells in DMEM containing 0.1% BSA) were allowed to bind in the presence or absence of the reference NANOBODY® or AU/VWFa-11 (1.25 µM). Binding of these cells was monitored by measuring the intrinsic alkaline phosphatase activity of the cells and set to be 100% in the absence of antibodies. Data represent the mean±SEM of 3 experiments. FIGS. 3B-D: Whole blood was perfused over coverslips coated with collagen type III (30 µg/cm$^2$ in 0.05 mol/l acetic acid) in the absence (FIG. 3B) or presence of the reference NANOBODY® (31.3 or 125 nM, FIG. 3C) or AU/VWFa-11 (62.5 or 625 nM, FIG. 3D) at a shear rate of 1600 s$^{-1}$. FIG. 3E/FIG. 3F: Reconstituted blood was perfused over coverslips coated with pd-VWF (15 µg/ml) in the absence (FIG. 3E) or presence of 625 nM AU/VWFa-11 (FIG. 3F) at a shear rate of 1600 s$^{-1}$. After perfusion adhered platelets were fixed in 0.5% glutaraldehyde in PBS, dehydrated in methanol and stained with May-Grünwald and Giemsa. FIG. 3G: Platelet adhesion was evaluated using computer-assisted analysis and was expressed as the percentage of surface covered with platelets (n=3).

Figure 4:
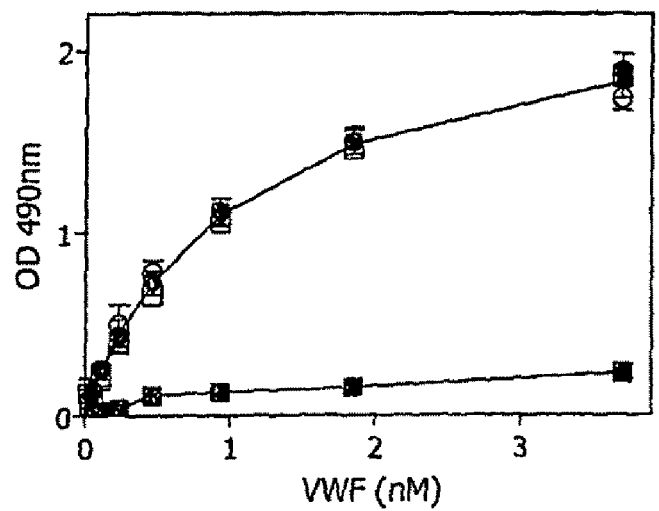

FIG. 4 is a graph showing the effect of ristocetin and the R1306Q mutation on binding to AU/VWFa-11. Microtiter wells were coated overnight at 37° C. with AU/VWFa-11 (5 μg/ml in 50 mM NaHCO$_3$, pH 9.6) and blocked 30 min at 37° C. with 3% BSA, 0.1% TWEEN-20™ (polysorbate 20) in PBS. After washing, microtiter wells were incubated with medium containing different concentrations of wt-VWF (squares) or VWF/R1306Q (circles) (0-3.7 nM). Binding was allowed for 1 h at 37° C. in the presence (open symbols) or absence (closed symbols) of 1 mg/ml ristocetin. Microtiter wells were washed using 0.1% TWEEN-20™ (polysorbate 20) in PBS and incubated with HRP-conjugated polyclonal anti-VWF antibody. Bound VWF was detected by measuring peroxidase activity. Data represent the mean±SD of 3 experiments.

Figure 5:
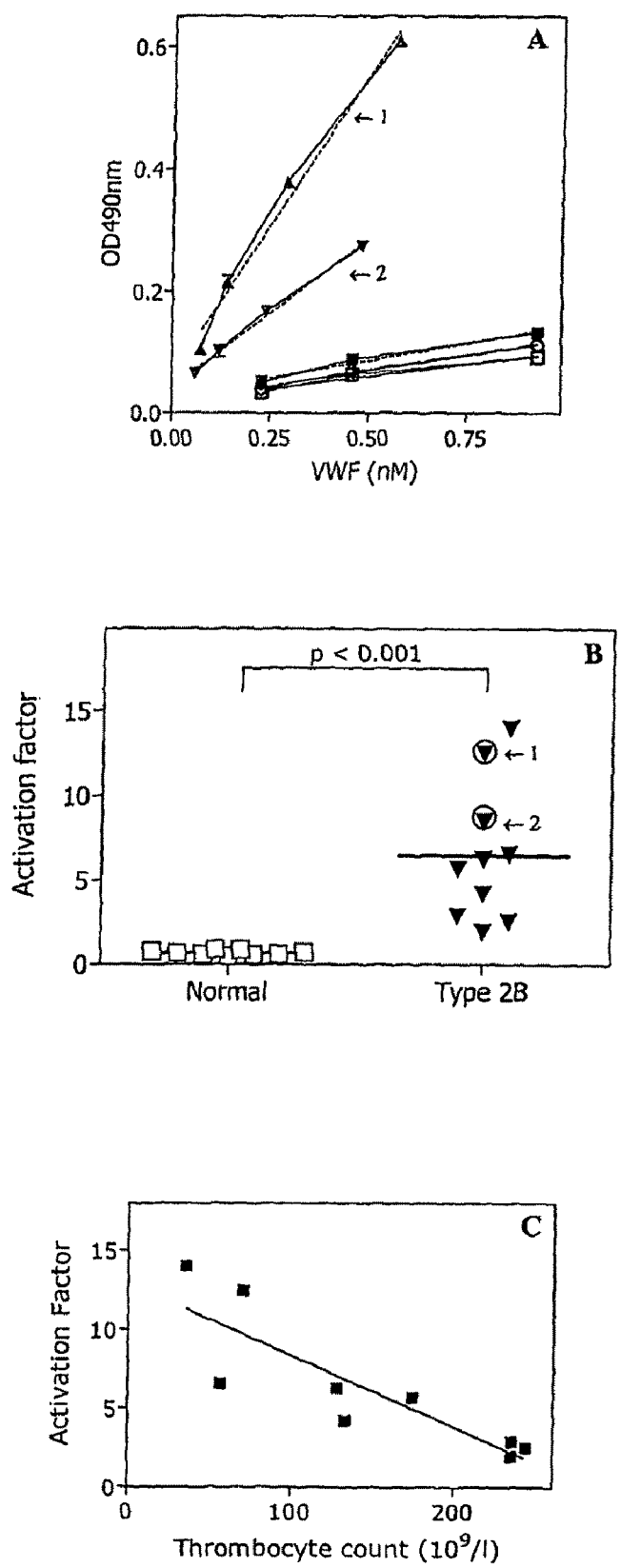

FIG. 5 is a graph showing activated VWF present in VWD type 2B plasma. FIG. 5A: Microtiter wells coated with AU/VWFa-11 (5 μg/ml) were blocked 30 min with 3% BSA, 0.1% Tween-20 in PBS. NPP (■), plasma from normal individuals (n=9, open symbols) and VWD type 2B plasma (n=12, triangles) were diluted in PBS to obtain a concentration range (0.23-0.93 nM). After washing, wells were incubated 1 h at 37° C. with the diluted plasmas. Bound VWF was detected using HRP-conjugated polyclonal anti-VWF antibody. The concentration of VWF in the diluted samples was plotted against the measured OD490 nm. The slope found for NPP was set to be 1. Arrows indicate the slopes found for two different VWD type 2B patients. Data represent the mean±SD of 2 experiments. FIG. 5B: The activation factors were calculated using equation 1 and plotted in a scatter plot. Arrows indicate the activation factors calculated for patient 1 and 2 from figure A. The activation factor found for VWD type 2B patients was significantly higher than for the normal individuals ($p<0.001$). Data represent the mean±SD of 2 experiments. FIG. 5C: The activation factor calculated for 9 VWD type 2B patients was plotted against the thrombocyte counts in these samples and a correlation was found to be significant ($p<0.003$, $R^2=0.7401$).

Figure 6:
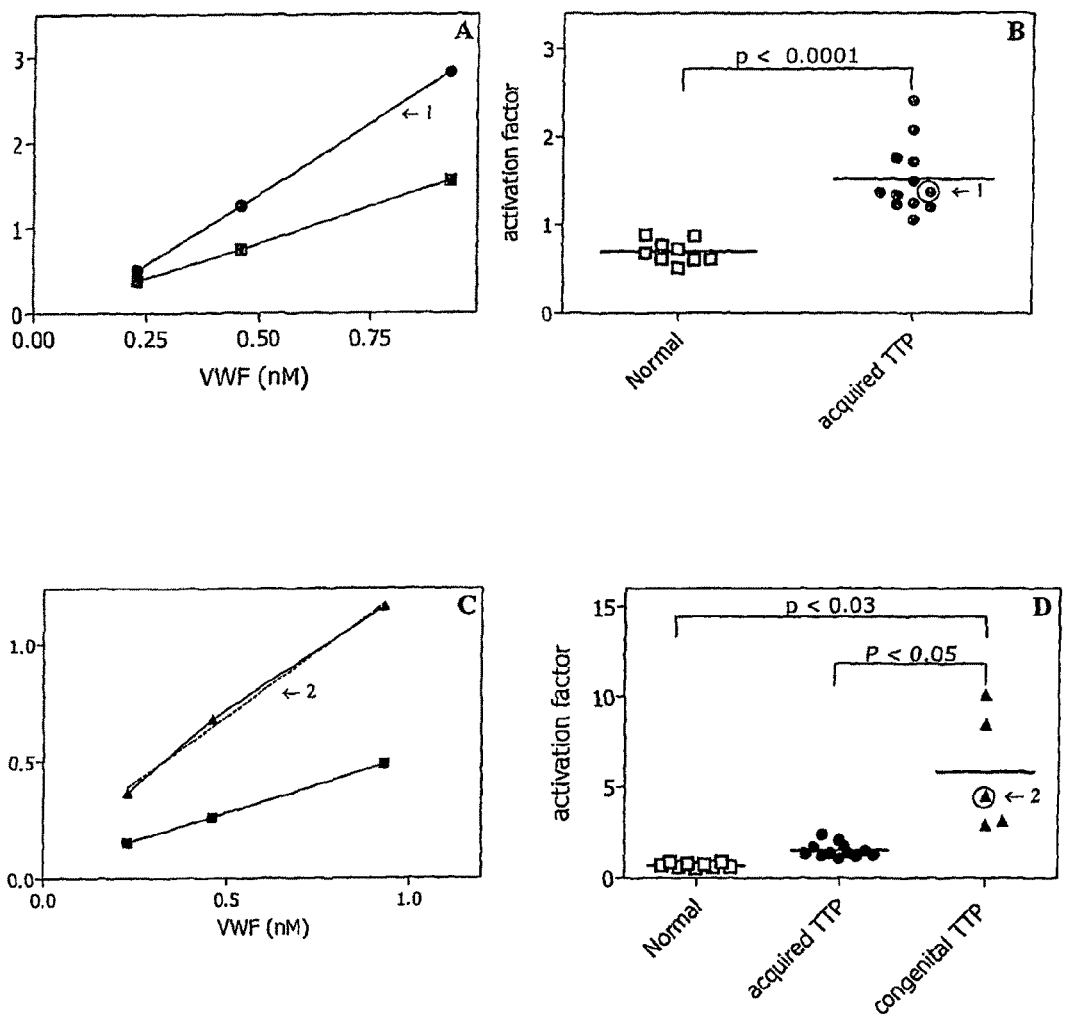

FIG. 6 is a graph showing detection of activated VWF in TTP plasma. FIG. 6A/FIG. 6C: AU/VWFa-11 coated microtiter wells were incubated with NPP (■), plasma from normal individuals (n=9, □) and plasma from patients suffering from acquired TTP (FIG. 6A, n=12, ●) or congenital TTP (FIG. 6C, n=5, ▲). Plasma was diluted before incubation to obtain a concentration range of VWF (62-250 ng/ml). Bound VWF was monitored with HRP-conjugated anti-VWF antibody. The amount of VWF in the diluted sample was plotted against the HRP activity (OD490 nm). Slopes were calculated and the slope found for NPP was set to be 1. Arrows indicate the slopes found for a patient suffering from acquired TTP (1) or congenital TTP (2). FIG. 6B/FIG. 6D: The activation factor was calculated and plotted in a scatter plot. Arrows indicate the values found for the patients plotted in FIG. 6A and FIG. 6C. Activation factors found for acquired and congenital TTP were significantly higher than for the normal individuals (acquired TTP vs. normal: $p<0.0001$ and congenital TTP vs. normal $p<0.03$). The activation factor found for congenital TTP was also significantly elevated when compared to acquired TTP ($p<0.05$). Data represent the mean±SD of 2 experiments.

Figure 7:
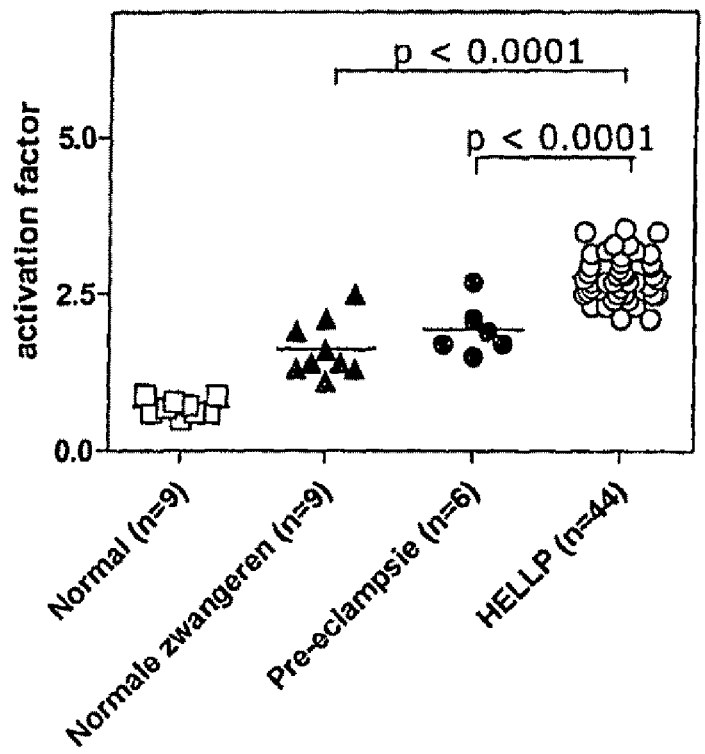

FIG. 7 is a graph showing elevated levels of active VWF in HELLP syndrome. NPP, samples of normal individuals (n=9, □) and normal pregnant controls (n=9, ▲; "Normale zwangeren"), samples of patients suffering from preeclampsia (n=6, ●; "Pre-eclampsie") and of patients with HELLP syndrome (n=44, ○) were diluted in PBS to reach a concentration range of VWF (250-31.5 ng/ml). Diluted samples were incubated 1 h at 37° C. in AU/VWFa-11 coated wells (5 μg/ml, coated overnight at 4° C. 50 mM NaHCO$_3$, pH 9.6, overnight at 4° C.). Bound VWF was detected with HRP-conjugated polyclonal anti-VWF antibody. The amount of VWF in the diluted sample was plotted against the HRP activity (OD490 nm). Slopes were calculated and the slope found for NPP was set to be 1. Data represent the mean±SD of 2 experiments.

EXPERIMENTAL PART

Platelets and Von Willebrand Factor coexist in circulation, but interaction only occurs at sites of injury. At these sites, VWF functions as a molecular bridge between the exposed subendothelial matrix and the GpIb-IX-V complex on platelets. A shift in the A1-domain of VWF to a GpIb-binding conformation is required for this interaction. In the present paper, llama antibody variable domain ("NANOBODY®") AU/VWFa-11 is discussed, that can distinguish between the non-binding and the binding conformation of VWF. This antibody variable domain recognizes a site in the A1 domain that is only exposed upon activation of VWF. The affinity of AU/VWFa-11 for the isolated A1 domain was found to be 77 nM, but introduction of Von Willebrand Disease type 2B mutation R1306Q, or incubation with ristocetin increased the binding efficiency. Using AU/VWFa-11, the conformation of VWF in plasma of VWD type 2B and Thrombotic Thrombocytopenic Purpura (TTP) patients was studied. Although, these diseases have different phenotypical appearances, both are characterized by thrombocytopenia, caused by spontaneous platelet-VWF interaction. Plasma of VWD type 2B and TTP patients contained significantly increased levels of activated VWF (resp. $p<0.001$ and $p<0.0001$). Moreover, in VWD type 2B patients an inverse correlation was found between the amount of activated VWF and the platelet number. VWF from patients with the congenital form of TTP was significantly more activated than VWF from acquired TTP patients ($p<0.05$). In conclusion, an AU/VWFa-11 immunosorbent assay could be used for the detection of TTP and to distinguish between acquired and congenital TTP. It also could provide a tool to investigate the role of VWF in other diseases.

Adhesion of platelets to the injured vessel wall is a multistep process, involving several components, including von Willebrand Factor (VWF). VWF is an adhesive glycoprotein that circulates in plasma as an array of multimeric subunits.[1] This multimeric structure allows VWF to function as a molecular bridge between the subendothelial matrix and the platelet-surface Glycoprotein (Gp) Ib/IX/V complex. Complex formation between VWF and the GpIb/IX/V receptor is of particular importance for the tethering of platelets on vascular surfaces exposed to rapidly flowing blood.[2]

The interaction between VWF and the GpIb/IX/V complex is mediated by specific regions of both components: VWF residues 1238-1481 (the so-called A1 domain) comprises an interactive site for residues 1-290 of GpIbα.[3] Although, the structure of this complex has been solved at the atomic level[4], some issues regarding this interaction have remained unclear. For instance, despite the notion that VWF and GpIbα coexist in the circulation, their interaction does not occur under normal conditions. In contrast, the isolated recombinant A1 domain does display spontaneous binding to GpIbα. Apparently, a shift from a non-binding to a binding mode of the VWF A1 domain in its multimeric environment is required to induce complex formation.[4] However, the molecular basis of this activation-step is largely unknown.

Activation of the A1 domain can be induced by several means. Non-physiological activation of the A1 domain occurs through direct immobilisation of purified VWF onto artificial surfaces, such as glass or plastic. In vitro activation of VWF is also achieved by the addition of modulators, such as the snake-venom component botrocetin or the antibiotic ristocetin.[5,6] Furthermore, physiological activation of VWF is induced upon its binding to the subendothelial matrix component collagen, or under conditions of very high shear stress. Also various pathological conditions may lead to premature complex formation between VWF and platelet GpIbα. Some gain-of-function mutations in the VWF A1 domain may increase the affinity for GpIbα. Such mutations are associated with von Willebrand disease type 2B, the patients of which are characterized by loss of high molecular weight multimers from plasma, increased ristocetin induced platelet aggregation, a prolonged bleeding time and thrombocytopenia.[7,8] Another condition that has been reported to allow spontaneous platelet adhesion relates to the size of multimeric VWF. Multimeric VWF is stored in Weibel-Palade bodies in endothelial cells, and released upon stimulation.[9-11] The newly released VWF is enriched in ultra-large (UL)-VWF multimers, which have the potential to bind platelets in the absence of any modulators.[12] Direct release of the UL-VWF molecules in the circulation is prevented by proteolysis of these multimers at the endothelial surface.[13] This process is mediated by the recently identified protease ADAMTS-13, which cleaves mature VWF between residues Met1605 and Tyr1606.[14,15] Once cleaved by ADAMTS-13, the residual multimers have lost the ability to bind platelets spontaneously. The importance of ADAMTS-13 activity is illustrated by the life-threatening disease Thrombotic Thrombocytopenic Purpura (TTP), in which ADAMTS-13 activity is low or absent. ADAMTS-13 deficiency is caused by inhibiting antibodies (acquired TTP)[16] or by mutations in the gene encoding ADAMTS-13 (congenital TTP)[17,18]. In the absence of ADAMTS-13 activity, an excess of UL-VWF multimers is released into the circulation, which leads to spontaneous platelet binding and subsequent thrombus formation in the microvasculature.[19] This causes haemolytic anemia, renal failure, neurological deficits, fever and sometimes coma.[20]

Although VWD type 2B and TTP are associated with different phenotypic appearances, they have in common that at least part of the circulating VWF multimers should exist in an active conformation. The presence of activated VWF can be determined indirectly by measuring ristocetin dependent platelet aggregation. However, this method is insensitive and can not be used when the VWF antigen is low. Herein, a llama-derived monoclonal antibody variable domain is described that recognizes immobilized VWF but not native VWF, suggesting that this antibody variable domain recognizes an epitope within the VWF A1 domain that becomes exposed upon activation of VWF. This antibody variable domain was subsequently used to monitor the presence of activated VWF in plasma samples of VWD type 2B and TTP patients. This analysis revealed that in the circulation of both patient groups the levels of activated VWF are elevated 2-10 fold compared to normal individuals.

Materials and Methods
Proteins and Antibodies.

Recombinant GpIbα (residues 1-290) was expressed and purified as described.[4] The GpIbα antibody (2D4) was a kind gift of Dr. H. Deckmyn (Kortrijk, Belgium). Botrocetin was purchased from Kordia laboratory supplies (Leiden, The Netherlands). Plasma derived (pd)-VWF was purified from cryoprecipitate (Haemate P 250 IE, Behringwerke AG, Marburg, Germany) as described.[21] Bovine serum albumin and human placental collagen type III were from Sigma and human albumin (Fraction V) was from MP Biochemicals (Irvine, Calif. USA). Polyclonal antibodies against VWF and HRP-conjugated antibodies against VWF were obtained from Dakocytomation (Glostrup, Denmark).

Construction and Expression of Recombinant Proteins.

Construction of expression vector pNUT encoding wt-VWF and VWF/R1306Q was described previously.[22-24] VWF/A1(1261-1468) and VWF/A1(1261-1468)-R1306Q were cloned into expression vector pPIC9 and overexpressed in *Pichia pastoris*.[4] pNUT-VWF/A1(1238-1481) was constructed by generating a PCR product with forward primer 5'-GGATCCCAGGAGCCGGGAGGCCTGGTGG-3' and reverse primer 5'-GCGGCCGCCCCCGGGCCCACAGT-GACTTG-3', for which pNUT-VWF served as template. After sequence analysis, the BamHI-NotI fragment was ligated into a BamHI-NotI digested pNUT vector containing a C-terminal 6-histidine tag. Wt-VWF, VWF/R1306Q and VWF/A1(1238-1481) were stably expressed in baby hamster kidney-cells, that also overexpress furin for proper removal of the propeptide.[22] The full-length proteins were purified from conditioned serum-free medium as described.[25] VWF/A1 (1238-1481) was purified from expression medium using $Ni^{2+}$/NTA chromatography.[4] VWF/A1(1261-1468) and VWF/A1(1261-1468)-R1306Q were expressed in *Pichia pastoris* and purified on heparin sepharose, followed by gel filtration.[4] Analysis on SDS-PAGE showed that all recombinant proteins were purified to homogeneity. The multimeric structure of wt-VWF and VWF/R1306Q was analysed using 0.1% SDS, 1% agarose gel electrophoresis as described previously.[26]

Production and Selection of Antibody Variable Domains (NANOBODIES®).

Llama antibodies were raised by immunization with a wt-VWF preparation containing high molecular weight multimers. Immunization and library construction were performed as described.[27] For selection of antibody variable domains the wells of a maxisorp microtiter plate (NUNC, Denmark) were coated with 5 µg/ml VWF/A1(1238-1481) in 50 mM $NaHCO_3$ buffer (pH 9.6, overnight at 4° C.). After washing, the wells were blocked for 3 h at room temperature with PBS containing 1% casein (PBS-C) and incubated with the phages (2 h room temperature). Wells were washed 10 times with PBS and bound phages were eluted with 0.2 M glycin buffer (pH 2.4, 20 min at room temperature). The eluted phages were added to exponentially growing *E. coli* TG1-cells[28] and cells were plated onto LB-ampicilin. In the second round, phages were resuspended in 10 µg/ml recombinant wt-VWF before incubation in VWF/A1(1238-1481) coated microtiter wells. Wells were washed 7 times for 30 min with 10 µg/ml wt-VWF and bound phages were eluted and allowed to infect TG-1 cells. Expression was induced by adding 1 mM isopropyl-1-thio-β-D-galactopyranoside to a TG-1 cell culture (OD600 nm=0.5), periplasmic proteins were extracted as described[29] and analyzed for binding to coated VWF/A1(1238-1481) (2 µg/ml). Binding was detected with a polyclonal rabbit-anti-llama antibody (Dakocytomation) and an HRP-conjugated goat-anti-rabbit antibody (Ablynx, Zwijnaarde, Belgium). DNA of all positive clones was digested with HinfI and clones with different HinfI patterns were used to transform into the non-suppressor strain of *E. coli*, WK-6 cells.[27] Periplasmic samples were prepared as described and antibody variable domains were purified to homogeneity using $Ni^{2+}$/NTA resin.

Competition Assay.

The specificity of the interaction between AU/VWFa-11 and activated VWF was assessed in an immunosorbent assay, in which purified pd-VWF (3.7 nM) was immobilized in microtiter wells (Costar, Cambridge Mass., USA). Wells were blocked with PBS containing 3% BSA and 0.1% TWEEN-20™ (polysorbate 20) for 1 h at 37° C. and incubated with different concentrations of a reference NANOBODY® (in accordance with WO 04/062551) and biotinylatyted AU/VWFa-11 (0-625 nM) in PBS for 1 h at 37° C. Binding of the antibody variable domains was monitored with HRP-conjugated streptavidin and the antibody concentration at half maximum binding was determined. These concentrations were used in the competition assay, in which pd-VWF coated wells were incubated with either of the antibodies in the absence or presence of indicated concentrations of wt-VWF or wt-VWF preincubated with 1 mg/ml ristocetin (5 min at room temperature) (0-115 nM soluble VWF for the reference NANOBODY® and 0-38 nM for AU/VWFa-11). After washing, wells were incubated with HRP-conjugated streptavidin (Dakocytomation, Denmark) and binding was detected by measuring HRP-activity using o-phenylenediamine (OPD) as substrate.

Surface Plasmon Resonance Analysis.

Surface Plasmon Resonance (SPR) binding studies were performed using a Biacore 2000 system (Biacore AB, Uppsala, Sweden). AU/VWFa-11 was immobilized on a Biacore® CM5 sensor chip using the amine-coupling kit as instructed by the supplier (Biacore AB, Uppsala, Sweden). V128H, a NANOBODY® recognizing the A3 domain of VWF, was used as a control. Binding of VWF/A1(1238-1281), VWF/A1(1261-1468) and VWF/A1(1261-1468)-R1306Q (a type 2B mutation) to the AU/VWFa-11 coated channel was corrected for binding to the V128H coated channel. Binding of VWF constructs to the immobilized NANOBODIES® was performed in 150 mM NaCl, 25 nM Hepes, 0.005% TWEEN-20™ (polysorbate 20) (pH 7.4) at 25° C. with a flow rate of 5 µl/min. Regeneration of the surface was performed by subsequent application of 50 mM triethyl amine and formate buffer (10 mM NaHCO$_2$ and 150 mM NaCl pH 2.0).

Static Adhesion of CHO-Cells Expressing the GpIb-IX-V Complex to Immobilized VWF.

Wt-VWF (37 nM) was immobilized overnight at 4° C. in microtiter wells (Nunclon, NUNC, Denmark) in 50 mM NaHCO$_3$ (pH 9.6). Wells were blocked with 0.5% PVP in PBS for 1 h at room temperature and incubated with 1.25 µM AU/VWFa-11 or reference NANOBODY® (1 h at room temperature). After washing three times with PBS, CHO-cells expressing the GpIb-IX-V complex (generous gift of Dr. Lopez), 1×10$^5$ cells in DMEM containing 0.1% BSA were allowed to bind to immobilized VWF (90 min at 37° C.) in the presence or absence of the reference NANOBODY® or AU/VWFa-11 (1.25 µM). Wells were washed and binding of cells was detected by measuring the intrinsic alkalic phophatase activity of the CHO-cells, using p-nitrophenyl phosphate (PNP, Sigma) as a substrate diluted in lysisbuffer (3 mg/ml PNP in 1% Triton-X-100, 50 mM acetic acid, pH 5.0).

Platelet Adhesion to Collagen Type III and VWF.

Perfusions over collagen type III were carried out with whole blood, drawn from healthy volunteers who denied ingestion of aspirin or other nonsteroidal anti-inflammatory drugs for the preceding 10 days, into 0.1 volume of 50 µg/ml PPACK (H-D-Phe-Pro-Arg-Chloromethylketone, Bachem, Torrence, Calif. USA) and 20 U/ml Pentasaccharide. Thermanox coverslips (NUNC, Denmark) were coated with collagen type III[30] and whole blood was perfused over the coverslips for 5 min at 1600 s$^{-1}$. Perfusions over VWF coated coverslips was performed with reconstituted blood at a shear rate of 1600 s$^{-1}$ as described.[30] After perfusion, slides were washed, fixed and stained[30] and platelet adhesion was evaluated using computer assisted analysis with OPTIMAS 6.0 software (Dutch Vision Systems BV, Breda, The Netherlands). All perfusions were performed 3 times.

Patient Materials.

Plasma samples of healthy donors (n=9), patients with VWD type 2B (n=10) and patients with acquired (n=12) or congenital TTP (n=5) were collected in 3.1% citrate using a vacutainer system. VWD type 2B was diagnosed in families with the typical pattern of an autosomal inherited bleeding disorder with thrombocytopenia, high ristocetin induced platelet aggregation and the absence of high multimeric VWF multimers on gel electrophoresis. Patients with acquired thrombotic thrombocytopenic purpura were characterized by thrombocytopenia, Coombs negative hemolytic anemia and the presence of fragmented erythrocytes in peripheral blood. Other causes for hemolytic anemia and thrombocytopenia were excluded and all patients were treated with plasma exchange. Response to plasma exchange was observed in all patients. Plasma samples were taken before treatment and ADAMTS-13 activity was found to be absent in these samples. Plasma samples of five patients with a congenital form of TTP were kindly provided by Dr. J. P. Girma (Hopital de Bicêtre, Paris, France). Platelet poor plasma (PPP) was aliquoted and frozen at −80° C. For normal pool plasma (NPP) PPP of 40 healthy donors was pooled and was stored in aliquots at −80° C. All patients gave informed consent for the sampling of blood for scientific purposes.

Immunosorbent Assay for Activated KWF.

VWF antigen levels were quantified as described before. Microtiter wells (Maxisorb, NUNC, Denmark) were coated overnight at 4° C. with 5 µg/ml AU/VWFa-11 in 50 mM NaHCO$_3$ (pH 9.6) and blocked with PBS containing 3% BSA and 0.1% TWEEN-20™ (polysorbate 20) for 30 min at 37° C. Wells were washed 3 times with PBS containing 0.1% TWEEN-20™ (polysorbate 20) and incubated with culture medium containing wt-VWF or VWF-R1306Q, or plasma samples (1 h 37° C.). All samples were diluted in PBS to reach a VWF concentration between 0.23 and 1.85 nM. After washing three times with PBS TWEEN-20™ (polysorbate 20) plates were incubated with HRP-conjugated polyclonal anti-VWF (1.3 µg/ml) in PBS for 1 h at 37° C. Plates were washed 3 times with PBS TWEEN-20™ (polysorbate 20) and binding was detected by measuring the HRP-activity using o-phenylenediamine as a substrate (Merck, Germany). Normal pool plasma (NPP) was used as standard in every ELISA. The slope of the different plasma samples was compared with the slope found for NPP binding using equation 1. The factor calculated with equation 1 was called the activation factor.

$$(slope_{sample}/slope_{NPP}) = \text{activation factor} \quad \text{(Equation 1)}$$

Variation of the AU/VWFa-11 Immunosorbent Assay.

To determine the intra-experiment variation of the AU/VWFa-11 immunosorbent assay, AU/VWFa-11 coated wells of one microtiter plate were incubated with one sample (normal individual no. 7) 10 times. Moreover, sample no. 7 was measured in 10 different experiments to determine the inter-experiment variation. NPP was used as standard and the activation factor was calculated. The intra-experiment variation was 7.1% and the variation between different experiments was 13.7%.

Data Analysis and Statistics.

Analysis of SPR data and AU/VWFa-11 immunosorbent assay data were performed using Graph Pad Prism (GraphPad Prism version 4.0 for windows, GraphPad Software, San Diego, Calif.). Data were expressed as mean with standard deviation. An unpaired t-test with Welch correction was performed to compare the mean levels of activated VWF between the different patient groups. A p<0.05 was considered significant.

Results

NANOBODY® AU/VWFa-11 Specifically Recognizes the Active Conformation of VWF.

In order to obtain antibodies that predominantly recognize activated but not native VWF, a llama was immunized with purified VWF preparations that contained UL-VWF (multimer size exceeding 20 subunits). Subsequently, the antibody repertoire of the animal was cloned, and monoclonal antibody variable domains were selected for their ability to bind to immobilized VWF through phage-display technology. The anti-VWF antibody variable domains that were isolated through this procedure were then screened for binding to an immobilized recombinant A1 fragment. Of the variable domains that were obtained, two were selected for further analysis, AU/VWFa-11 and a reference NANOBODY®. Both domains were monitored for their ability to distinguish between native VWF and ristocetin-activated VWF. To this end, purified recombinant wt-VWF was immobilized in microtiter wells. This procedure leads to conformational changes in the molecule, allowing the binding of antibodies that are specific for activated VWF. As expected, both biotinylated antibodies bound to immobilized VWF in a dose-dependent and saturable manner. Half maximum binding was obtained at 62.5 nM for the reference NANOBODY®, or at 1.9 nM for AU/VWFa-11 (FIG. 1A/B). These concentrations were used in a competition assay, in which binding of the antibodies was studied in the presence of different concentrations of soluble wt-VWF or wt-VWF preincubated with ristocetin (FIG. 1B). The presence of an equal molar concentration of both competitors reduced binding of biotinylated reference NANOBODY® by ±90%. In contrast, binding of biotinylated AU/VWFa-11 remained unaffected in the presence of a 20-fold molar excess of wt-VWF, whereas ristocetin-activated VWF interfered with binding in a dose-dependent manner. Apparently AU/VWFa-11 has the potential to selectively recognize VWF that is, at least in part, in an activated conformation.

AU/VWFa-11 Recognizes Epitope in A1 Domain

The interaction between NANOBODY® AU/VWFa-11 and the A1 domain of VWF was then investigated in more detail. First, the interaction between AU/VWFa-11 and VWF/A1(1238-1481) was monitored in a quantitative manner using SPR analysis. Various concentrations of VWF/A1(1238-1481) (0-500 nM) were perfused over immobilized AU/VWFa-11 (0.08 pmol/mm$^2$) at a flow rate of 20 µl/min. VWF/A1(1238-1481) associated to the immobilized NANOBODY® in a dose-dependent, saturable and reversible manner (FIG. 2A). Equilibrium-based analysis of the binding for isolated A1 domain to immobilized AU/VWFa-11 revealed an affinity constant of 77 nM. In an alternative approach, the binding of NANOBODY® AU/VWFa-11 to three variants of the A1 domain: VWF/A1(1238-1481) (which includes flanking regions of the A1 domain), VWF/A1(1261-1468) (which lacks the flanking regions) and VWF/A1(1261-1468)-R1306Q (containing the type 2B mutation Arg1306 to Gln) was compared. All three VWF/A1 domains were perfused over an AU/VWFa-11 coated Biacore® CM5 sensor chip (0.12 pmol/mm$^2$) at a flowrate of 5 µl/min and were bound by the NANOBODY® (FIG. 2B). Perfusion of VWF/A1(1261-1468) over the AU/VWFa-11 coated chip resulted in a higher signal than perfusion of VWF/A1(1238-1481). Moreover, VWF/A1(1261-1468)-R1306Q was bound more efficiently than VWF/A1(1261-1468). These results may suggest that exposure of the epitope of NANOBODY® AU/VWFa-11 indeed relies on the activation of the A1 domain.

GpIb and AU/VWFa-11 Bind Different Regions Within the A1 Domain

The conformation induced by ristocetin, immobilization of VWF, or a VWD type 2B mutation, promotes binding to GpIbα and this conformation is also specifically recognized by AU/VWFa-11. Therefore, the possibility was considered that AU/VWFa-11 and GpIbα bind to similar regions in the A1 domain. This was first tested in a static adhesion assay, in which CHO-cells expressing the GpIb-IX-V complex were allowed to bind to immobilized wt-VWF in the presence or absence of the above reference NANOBODY® or the NANOBODY® AU/VWFa-11. As expected, the CHO-cells bound efficiently to immobilized VWF (FIG. 3A), confirming that immobilization of VWF induces the shift to a GpIb-binding conformation. This interaction was partially inhibited (up to 59%) by 1.25 µM of the reference NANOBODY®. In contrast, even in the presence of 1.25 µM AU/VWFa-11, binding of the CHO-cells to immobilized VWF remained unaffected, suggesting that the binding site for AU/VWFa-11 is distinct from the binding site for GpIbα.

Since the effect of both NANOBODIES® on the binding of VWF to GpIbα may be different under flow conditions, their effect in a perfusion assay was studied. Human whole blood was perfused over a collagen type III surface at high shear (1600 s$^{-1}$). Under these conditions, platelet adhesion is fully dependent on the interaction between VWF and GpIbα.[31] In the absence of NANOBODIES®, these conditions resulted in a platelet coverage of 67.8±8.3% (n=3)(FIG. 3B). The presence of the reference NANOBODY® was associated with a decreased platelet coverage (49.8±4.5 and 24.9±3.1% in the presence of 31.3 and 125 nM antibody, respectively) (FIG. 3C). In contrast, even in the presence of 625 nM antibody AU/VWFa-11, platelet coverage was still similar to that in its absence (73.3±4.4%, FIG. 3D). Moreover, platelet adhesion to a VWF-surface remained unaffected in the presence of AU/VWFa-11 (FIG. 3E/F). These data are compatible with the view that GpIbα and antibody AU/VWFa-11 bind to different regions of the A1 domain.

Immunosorbent Assay for Detection of Activated vWF in Solution

Although GpIbα and NANOBODY® AU/VWFa-11 bind to distinct sites within VWF, both have in common that they only recognize VWF in its activated form, which is for instance induced by immobilization, ristocetin or VWD type 2B mutations. This unique feature makes it possible to use this antibody for the detection of activated VWF in solution. As a first example, the binding of recombinant wt-VWF and recombinant VWF/R1306Q to immobilized NANOBODY® AU/VWFa-11 was compared. Therefore, this particular NANOBODY® was immobilized in microtiter wells, and incubated with various concentrations (0-3.7 nM) of wt-VWF and VWF/R1306Q in the absence and presence of ristocetin. The amount of bound VWF was subsequently monitored using HRP-conjugated polyclonal antibodies against VWF. With regard to wt-VWF, some binding could be observed, but absorbance values remained below 0.3 (FIG. 4). The addition of ristocetin resulted in a strong increase in binding, represented by a 6-fold increase in absorbance (up to 1.85). This difference was quantified by calculating the respective slopes of the initial, linear parts of the curve. This revealed that the slope for VWF/ristocetin was increased 2.7 fold compared to wt-VWF alone. A similar increase in slope compared to wt-VWF could be observed for VWF/R1306Q in the absence of ristocetin (FIG. 4). Moreover, this increase was not further enhanced in the presence of ristocetin. Apparently, this assay provides a useful tool to detect circulating VWF containing an A1 domain in active conformation.

Detection of Activated vWF in Patient Plasma

Since NANOBODY® AU/VWFa-11 was particularly efficient in the detection of active VWF in solution, it was tested whether this NANOBODY® could be used for the detection of active VWF in plasma of patients. First, the plasma of patients previously defined as type 2B was analyzed, as well as a group of normal individuals. As a reference, normal pooled plasma (NPP) was used (see materials and methods). The absorbance values obtained for NPP remained low (FIG. 5A), and the slope was set to be 1. Also for each of the normal individuals, only low absorbance values were detected, suggesting low amounts of active VWF in their plasma (FIG. 5A). The mean slope compared to NPP was 0.70±0.13 (n=9; FIG. 5B). In contrast, high amounts of active VWF could be determined in the plasmas of the VWD type 2B patients, as illustrated by the strongly increased absorbance values (FIG. 5A). The mean slope of was calculated to be 8.4±4.5 (n=10; p=0.0006 compared to normal individuals; FIG. 5B). Thus, this assay indeed seems to be useful to analyze the presence of active VWF in plasma of patients.

Correlation between VWF Activation and Platelet Count

Interestingly, the activation factor determined for VWF in plasma of VWD type 2B patients, varied considerably (1.95-14.0). This variation was not found in plasma of normal individuals (0.51-0.89). VWF containing type 2B mutations binds spontaneously to platelets, leading to enhanced clearance of both platelets and VWF. Therefore, the possibility was considered that the relative activation of VWF in circulation influenced the formation of platelet-VWF complexes. To address this question, the platelet count in the different plasma samples was measured and plotted this against the activation factor. A strong inverse correlation was found between these parameters (FIG. 5C, $p<0.003$, $R^2=0.7401$).

Detection of Active VWF in Plasma of TTP Patients

A second group of patients that was analyzed for the presence of active VWF in their plasma were patients lacking ADAMTS-13 activity, which was clinically manifested as TTP. Two groups could be distinguished: one group was defined as patients having a congenital deficiency of ADAMTS-13 (n=5), whereas a second group had an acquired deficiency of ADAMTS-13 (n=12). Compared to the group of normal individuals (see above), patients having acquired ADAMTS-13 deficiency appeared to have increased levels of active VWF in their plasma. The mean slope was calculated to be 1.52±0.40 (p<0.0001), which is significantly higher compared to the group of normal individuals. Also the patients with congenital ADAMTS-13 deficiency contained active VWF in their plasma. Interestingly, the amount of active VWF (slope=5.85±3.3) was increased not only compared to the normal individuals (p<0.03), but also compared to the acquired ADAMTS-13-deficient patients (p<0.05). Moreover, no overlap in slope values was observed between each of the normal individuals and the two patient groups. This suggests that the assay may be useful for the diagnosis of ADAMTS-13 deficiency in that it allows rapid distinguishing between acquired and congenital ADAMTS-13 deficiency.

VWF in the GpIb-Binding Conformation in HELLP Syndrome

A third pathological condition characterized by thrombocytopenia is HELLP syndrome (Haemolysis, Elevated Liver enzymes and Low Platelets). VWF antigen levels are increased during normal pregnancy and even more in patients suffering from preeclampsia and HELLP (hemolysis, elevated liver enzymes, and low platelets), which is considered to be a severe form of preeclampsia. HELLP is characterized by a consumptive thrombocytopenia and is a risk for maternal and neonatal morbidity and mortality. Binding of VWF to AU/VWFa-11 was analysed in an immunosorbent assay for normal pregnant controls (n=9), patients with preeclampsia (n=6) and patients during HELLP syndrome (n=44) The activation factor calculated for patients with preeclampsia was not significantly elevated compared to the healthy pregnant controls. However, in patients suffering from HELLP syndrome the level of activated VWF was significantly increased compared to normal pregnant controls (p<0.0001) and compared to patients with preeclampsia (p<0.0001). The VWF-activation factor correlated significantly with both VWF antigen levels and with VWF ristocetin cofactor activity measured in the same samples. (Spearman's rank correlation coefficient 0.908, p<0.0001).

Discussion

During the adhesion of platelets to the injured vessel wall, VWF functions as a molecular bridge between the exposed subendothelial matrix and the GpIb-IX-V complex. For the interaction between GpIbα and the A1 domain of VWF, activation by a shift from a non-binding to a binding mode is required. Although under various pathological conditions, such as VWD type 2B and TTP, spontaneous interaction between VWF and platelets occurs, so far no assay has been developed to detect the presence of such activated VWF molecules directly in plasma Herein, antibodies and variable domains thereof are described that are able to distinguish between the resting and the activated state of VWF. Using this antibody, it was shown that activated VWF circulates in plasma of patients with VWD type 2B and TTP.

To develop an antibody that could distinguish between the GpIb-binding and non-binding conformation of VWF, llamas were immunized with recombinant wt-VWF. Llamas produce a substantial proportion of their functional immunoglobulins as homodimers of heavy chains lacking light chains.[32] These antibodies are small (16 kD) and have been reported to react specifically and with high affinity to their antigens.[27] Moreover, it is relatively easy to generate a library and screen many antibodies using phage display technology. This procedure resulted in a NANOBODY®, AU/VWFa-11, that was found to specifically recognize the A1 domain if VWF was preincubated with ristocetin (FIG. 1). The binding site for AU/VWFa-11 in the A1 domain of VWF was also exposed when a VWD type 2B mutation, R1306Q, was introduced (FIGS. 2B and 4). Dumas et al[33] have shown in a model that the R1306Q mutation induces a conformational change, which results in a strong and spontaneous interaction with GpIb. This may suggest that AU/VWFa-11 binds a region that is only exposed when VWF is in a GpIb binding conformation.

We considered the possibility that AU/VWFa-11 recognizes a region within the GpIbα-binding site. However, botrocetin-induced binding of VWF to recombinant GpIbα was not affected by an excess of AU/VWFa-11. Moreover, binding of CHO-cells expressing the GpIb-IX-V complex to immobilized VWF and binding of platelets to collagen type III, or VWF under flow conditions, remained unchanged in the presence of an excess of the NANOBODY®. These observations suggest that GpIbα and AU/VWFa-11 bind to different sites in the A1 domain, or that the affinity of GpIbα for its binding site is higher that the affinity of AU/VWFa-11. The latter is unlikely, since it is known that llama antibodies bind with high affinity to their antigens.[27]

In an attempt to further identify the binding site for AU/VWFa-11, binding of two different A1 domains to the antibody domain was studied. The A1 domain used for selection of the antibodies, VWF/A1(1238-1481), also contained the N- and C-terminal flanking peptides of the A1 domain. SPR analysis revealed that removal of these flanking peptides improved exposure of the binding site for AU/VWFa-11 (FIG. 2B). Since AU/VWFa-11 is specific for the GpIb-binding conformation of VWF, this result suggests that the flanking regions of the A1 domain play a role in the shift from the non-binding to the binding conformation. These results are in agreement with the report of Nakayama et al[34] that suggests that the flanking peptides influence the interaction between GpIbα and VWF.

Thus far, ristocetin induced platelet activation is often used to measure the GpIb-binding capacity of VWF. This assay is able to measure the reactivity of plasma VWF, but is based on non-physiological, ristocetin-induced, aggregation. AU/VWFa-11 was specifically designed to distinguish between native VWF and VWF in the GpIb-binding conformation. Only very low amounts of VWF are required to measure the activity, which makes the AU/VWFa-11 based immunosorbent assay suitable to measure the conformational state of VWF in diseases with low VWF antigen levels, such as TTP. Moreover, AU/VWFa-11 recognizes a site that is exposed upon activation, which can be induced in various ways, such as immobilization of VWF, incubation with ristocetin, or VWD type 2B mutations. This makes the AU/VWFa-11 immunosorbent assay very useful to study the conformational state of VWF under different pathological conditions.

The unique feature of AU/VWFa-11 to distinguish between the GpIb-binding and non-binding conformation of VWF makes it possible to study VWF in plasmas of healthy individuals and patients suffering from VWD type 2B and TTP. Plasma of healthy individuals and NPP showed only little binding of VWF to immobilized AU/VWFa-11, suggesting that the majority of the circulating VWF is in a non-binding conformation. Some residual binding was found, indicating that even under physiological conditions a minor proportion of the VWF molecules circulates in an activated conformation.

Subsequently, the activation factor of VWF in VWD type 2B and TTP was measured.
These two phenotypically distinct diseases are both characterized by thrombocytopenia, caused by spontaneous platelet-VWF interaction. In both diseases, significantly increased levels of activated VWF were found, compared to normal individuals (FIGS. 5 and 6). Moreover, an inverse correlation was found between the activation measured for VWF in plasma of VWD type 2B patients and the platelet numbers (FIG. 5C). This indicates a direct role for activated VWF in the onset of thrombocytopenia.

Interestingly, when AU/VWFa-11 was incubated with plasma from congenital TTP patients, it was found that the activation factor was not only significantly elevated compared to normal individuals, but also compared to acquired TTP patients. Plasma samples of patients with acquired TTP were collected upon admission into hospital, before treatment with plasma exchange. At this time, a substantial part of the activated VWF could be present in the platelet rich thrombi found in the microvasculature. This could explain the differences in levels of activated VWF between acquired and congenital TTP. On the other hand, the different molecular background of acquired and congenital TTP could also account for the difference in activation of VWF. Although further studies have to be performed, the AU/VWFa-11 immunosorbent assay seems a useful means to distinguish between acquired and congenital TTP.

In summary, the new NANOBODY® described herein is able to discriminate between the resting and activated state of VWF. The AU/VWFa-11 immunosorbent assay makes it possible to detect activated VWF in plasma, which makes it a very useful means to investigate the role of VWF in different diseases.

REFERENCE LIST (1) Ruggeri Z M. Von Willebrand factor. Curr Opin Hematol. 2003; 10:142-149.
(2) Savage B, Saldivar E, Ruggeri Z M. Initiation of platelet adhesion by arrest onto fibrinogen or translocation on von Willebrand factor. Cell. 1996; 84:289-297.
(3) Vicente V, Houghten R A, Ruggeri Z M. Identification of a site in the alpha chain of platelet glycoprotein Ib that participates in von Willebrand factor binding. J Biol Chem. 1990; 265:274-280.
(4) Huizinga E G, Tsuji S, Romijn R A et al. Structures of glycoprotein Ibalpha and its complex with von Willebrand factor A1 domain. Science. 2002; 297:1176-1179.
(5) Berndt M C, Du X P, Booth W J. Ristocetin-dependent reconstitution of binding of von Willebrand factor to purified human platelet membrane glycoprotein Ib-IX complex. Biochemistry. 1988; 27:633-640.
(6) Scott J P, Montgomery R R, Retzinger G S. Dimeric ristocetin flocculates proteins, binds to platelets, and mediates von Willebrand factor-dependent agglutination of platelets. J Biol Chem. 1991; 266:8149-8155.
(7) Ruggeri Z M, Pareti F I, Mannucci P M, Ciavarella N, Zimmerman T S. Heightened interaction between platelets and factor VIII/von Willebrand factor in a new subtype of von Willebrand's disease. N Engl J Med. 1980; 302:1047-1051.
(8) Ruggeri Z M, Zimmerman T S. von Willebrand factor and von Willebrand disease. Blood. 1987; 70:895-904.
(9) Ruggeri Z M, Ware J. The structure and function of von Willebrand factor. Thromb Haemost. 1992; 67:594-599.
(10) Sadler J E. Biochemistry and genetics of von Willebrand factor. Annu Rev Biochem. 1998; 67:395-424.
(11) Wagner D D, Marder V J. Biosynthesis of von Willebrand protein by human endothelial cells. Identification of a large precursor polypeptide chain. J Biol Chem. 1983; 258:2065-2067.
(12) Arya M, Anvari B, Romo G M et al. Ultralarge multimers of von Willebrand factor form spontaneous high-strength bonds with the platelet glycoprotein Ib-IX complex: studies using optical tweezers. Blood. 2002; 99:3971-3977.
(13) Dong J F, Moake J L, Nolasco L et al. ADAMTS-13 rapidly cleaves newly secreted ultralarge von Willebrand factor multimers on the endothelial surface under flowing conditions. Blood. 2002; 100:4033-4039.
(14) Fujikawa K, Suzuki H, McMullen B, Chung D. Purification of human von Willebrand factor-cleaving protease and its identification as a new member of the metalloproteinase family. Blood. 2001; 98:1662-1666.
(15) Gerritsen H E, Robles R, Lammle B, Furlan M. Partial amino acid sequence of purified von Willebrand factor-cleaving protease. Blood. 2001; 98:1654-1661.
(16) Moake J L. Thrombotic microangiopathies. N Engl J Med. 2002; 347:589-600.
(17) Levy G G, Nichols W C, Lian E C et al. Mutations in a member of the ADAMTS gene family cause thrombotic thrombocytopenic purpura. Nature. 2001; 413:488-494.
(18) Remuzzi G, Galbusera M, Noris M et al. von Willebrand factor cleaving protease (ADAMTS13) is deficient in

(19) Moake J L, Turner N A, Stathopoulos N A, Nolasco L H, Hellums J D. Involvement of large plasma von Willebrand factor (vWF) multimers and unusually large vWF forms derived from endothelial cells in shear stress-induced platelet aggregation. J Clin Invest. 1986; 78:1456-1461.

(20) George J N. How I treat patients with thrombotic thrombocytopenic purpura-hemolytic uremic syndrome. Blood. 2000; 96:1223-1229.

(21) Sodetz J M, Pizzo S V, McKee P A. Relationship of sialic acid to function and in vivo survival of human factor VIII/von Willebrand factor protein. J Biol Chem. 1977; 252: 5538-5546.

(22) Lankhof H, van Hoeij M, Schiphorst M E et al. A3 domain is essential for interaction of von Willebrand factor with collagen type III. Thromb Haemost. 1996; 75:950-958.

(23) Lankhof H, Damas C, Schiphorst M E et al. Functional studies on platelet adhesion with recombinant von Willebrand factor type 2B mutants R543Q and R543W under conditions of flow. Blood. 1997; 89:2766-2772.

(24) Sixma J J, Schiphorst M E, Verweij C L, Pannekoek H. Effect of deletion of the A1 domain of von Willebrand factor on its binding to heparin, collagen and platelets in the presence of ristocetin. Eur J Biochem. 1991; 196:369-375.

(25) Lenting P J, Westein E, Terraube V et al. An experimental model to study the in vivo survival of von Willebrand factor. Basic aspects and application to the R1205H mutation. J Biol Chem. 2004; 279:12102-12109.

(26) Romijn R A, Westein E, Bouma B et al. Mapping the collagen-binding site in the von Willebrand factor-A3 domain. J Biol Chem. 2003; 278:15035-15039.

(27) Arbabi G M, Desmyter A, Wyns L, Hamers R, Muyldermans S. Selection and identification of single domain antibody fragments from camel heavy-chain antibodies. FEBS Lett. 1997; 414:521-526.

(28) Hoogenboom H R, Griffiths A D, Johnson K S et al. Multi-subunit proteins on the surface of filamentous phage: methodologies for displaying antibody (Fab) heavy and light chains. Nucleic Acids Res. 1991; 19:4133-4137.

(29) Skerra A, Pluckthun A. Assembly of a functional immunoglobulin Fv fragment in *Escherichia coli*. Science. 1988; 240:1038-1041.

(30) Lisman T, Moschatsis S, Adelmeijer J, Nieuwenhuis H K, de Groot P G. Recombinant factor VIIa enhances deposition of platelets with congenital or acquired alpha IIb beta 3 deficiency to endothelial cell matrix and collagen under conditions of flow via tissue factor-independent thrombin generation. Blood. 2003; 101:1864-1870.

(31) Wu Y P, Vink T, Schiphorst M et al. Platelet thrombus formation on collagen at high shear rates is mediated by von Willebrand factor-glycoprotein Ib interaction and inhibited by von Willebrand factor-glycoprotein IIb/IIIa interaction. Arterioscler Thromb Vasc Biol. 2000; 20:1661-1667.

(32) Hamers-Casterman C, Atarhouch T, Muyldermans S et al. Naturally occurring antibodies devoid of light chains. Nature. 1993; 363:446-448.

(33) Dumas J J, Kumar R, McDonagh T et al. Crystal structure of the wild-type von Willebrand factor A1-glycoprotein Ibalpha complex reveals conformation differences with a complex bearing von Willebrand disease mutations. J Biol Chem. 2004; 279:23327-23334

(34) Nakayama T, Matsushita T, Dong Z et al. Identification of the regulatory elements of the human von Willebrand factor for binding to platelet GPIb. Importance of structural integrity of the regions flanked by the CYS1272-CYS1458 disulfide bond. J Biol Chem. 2002; 277:22063-22072.

The invention claimed is:

1. Method for distinguishing between different states or forms of diseases and disorders characterized by thrombocytopenia and/or by spontaneous interaction between Von Willebrand Factor (vWF) and platelets, and/or to predict the progression of such a disease or disorder, said method comprising the steps of:
  a) providing at least one biological sample obtained from a patient suffering from, or suspected to suffer from, at least one disease or disorder characterized by thrombocytopenia and/or by spontaneous interaction between Von Willebrand Factor (vWF) and platelets;
  b) determining the amount of vWF in a GpIb binding conformation in said biological sample;
  in which the amount of vWF in a GpIb binding conformation in the sample is representative for the different states or forms of the disease or disorder,
  in which the amount of vWF in the GpIb binding conformation is determined by contacting the biological sample with a binding agent that specifically binds vWF in the GpIb binding conformation in the presence of vWF in the non-GpIb binding conformation and then optionally determining the amount of vWF in the GpIb binding conformation bound to the binding agent.

2. Method according to claim 1, wherein said GpIb binding conformation is characterized by exposure of the A1 domain of vWF molecules, such that interaction between the vWF A1 domain and GpIb is facilitated/improved.

3. Method according to claim 1, in which the biological sample is a sample that contains vWF.

4. Method according to claim 1, in which the biological sample is a sample that contains vWF and platelets.

5. Method according to claim 1, in which the biological sample is chosen from whole blood, plasma, serum or other suitable blood fractions.

6. Method according to claim 4, in which both the amount of vWF in the GpIb binding conformation in the sample and the platelet number in the sample are determined, and optionally are compared to each other.

7. Method according to claim 1, in which the diseases and disorders characterized by thrombocytopenia and/or by spontaneous interaction between Von Willebrand Factor (vWF) and platelets are chosen from the group consisting of: Thrombocytopenic Purpura (TTP), pre-eclampsia, HELLP syndrome, Von Willebrand disease Type 2; DIC (diffuse intracellular coagulation) or Sepsis; malignant hypertension; antiphospholipid syndrome; exposure to carcinogens in general; after platelet transfusion with platelet concentrates (for perfusion).

8. Method according to claim 7, in which the disease characterized by thrombocytopenia and/or by spontaneous interaction between Von Willebrand Factor (vWF) and platelets is Thrombocytopenic Purpura (TTP) and which in the method is used to distinguish between patients with acquired TTP and patients with congenital TTP.

9. Method according to claim 7, in which the disease characterized by thrombocytopenia and/or by spontaneous interaction between Von Willebrand Factor (vWF) and platelets is pre-eclampsia or HELLP syndrome and in which the method is used to distinguish between patients with pre-eclampsia and patients with HELLP syndrome.

10. Method according to claim 7, in which the disease characterized by thrombocytopenia and/or by spontaneous interaction between Von Willebrand Factor (vWF) and platelets is pre-eclampsia and in which the method is used to predict the progress of said pre-eclampsia, and in particular to predict the which patients with pre-eclampsia will develop HELLP and/or determine which patients are at an increased risk of developing HELLP.

11. Method according to claim 1, in which the binding agent is a protein or polypeptide that is capable of specifically binding vWF in the GpIb binding conformation in the presence of vWF in the non-GpIb binding conformation.

12. Method according to claim 1, in which the binding agent is an antibody that is capable of specifically binding vWF in the GpIb binding conformation in the presence of vWF in the non-GpIb binding conformation; a part of fragment of an antibody, in which said part or fragment is capable of specifically binding vWF in the GpIb binding conformation in the presence of vWF in the non GpIb binding conformation; or a protein or polypeptide that contains one or more parts of fragments of an antibody, in which at least one of said parts or fragments is capable of specifically binding vWF in the GpIb binding conformation in the presence of vWF in the non GpIb binding conformation.

13. Method according to claim 1, in which the binding agent is a heavy chain antibody that is capable of specifically binding vWF in the GpIb binding conformation in the presence of vWF in the non-GpIb binding conformation; a part of fragment of a heavy chain antibody, in which said part or fragment is capable of specifically binding vWF in the GpIb binding conformation in the presence of vWF in the non-GpIb binding conformation; or a protein or polypeptide that contains one or more parts of fragments of a heavy chain antibody, in which at least one of said parts or fragments is capable of specifically binding vWF in the GpIb binding conformation in the presence of vWF in the non-GpIb binding conformation.

14. Method according to claim 1, in which the binding agent is a variable domain of antibody, in which said variable domain is capable of specifically binding vWF in the GpIb binding conformation in the presence of vWF in the non-GpIb binding conformation; or a protein or polypeptide that contains one or more variable domains, in which at least one of said variable domains is capable of specifically binding vWF in the GpIb binding conformation in the presence of vWF in the non GpIb binding conformation.

15. Method according to claim 14, in which at least one of said variable domains is a heavy chain variable domain.

16. Method according to claim 14, in which at least one of said variable domains is a variable domain of a heavy chain antibody.

17. Method according to claim 11, in which the binding agent is a NANOBODY® that specifically binds vWF in the GpIb binding conformation in the presence of vWF in the non-GpIb binding conformation; or a protein or polypeptide that contains one or more NANOBODIES®, in which at least one of said NANOBODIES® is capable of specifically binding vWF in the GpIb binding conformation in the presence of vWF in the non-GpIb binding conformation.

18. Method according to claim 1, in which the binding agent comprises AU/VWFa-11, a part of a fragment of AU/VWFa-11, or a protein or polypeptide comprising one or more parts of fragments of AU/VWFa-11.

19. Method according to claim 1, in which the amount of vWF in the GpIb binding conformation is determined by an immunosorbent assay involving the use of the binding agent.

20. Method according to claim 1, in which the binding agent is immobilized on a suitable support.

21. Kit-of-parts for determining the amount of vWF in the GpIb binding conformation in a sample, comprising at least a binding agent that is capable of specifically binding vWF in the GpIb binding conformation in the presence of vWF in the non-GpIb binding conformation; and optionally comprising means for determining the total amount of vWF in the GpIb binding and the non-GpIb binding conformation in the sample; and/or means for determining the platelet number in the sample; and/or instructions for use; and/or one or more parts, elements or components of kits for binding assays known per se; for distinguishing between different states or forms of diseases and disorders characterized by thrombocytopenia and/or by spontaneous interaction between vWF and platelets, and/or to predict the progression of such a disease or disorder, wherein said kit-of-parts is optionally packaged in a suitable packaging or container.

22. Kit-of-parts according to claim 21, wherein the binding agent is an antibody that is capable of specifically binding vWF in the GpIb binding conformation in the presence of vWF in the non-GpIb binding conformation; a part or fragment of an antibody, wherein said part or fragment is capable of specifically binding vWF in the GpIb binding conformation in the presence of vWF in the non-GpIb binding conformation; or a protein or polypeptide containing a part or fragment of an antibody, wherein said part or fragment is capable of specifically binding vWF in the GpIb binding conformation in the presence of vWF in the non-GpIb binding conformation.

23. Method according to claim 1, in which the binding agent comprises AU/VWFa-12, a part of a fragment of AU/VWFa-12, or a protein or polypeptide comprising one or more parts of fragments of AU/VWFa-12.

24. Method according to claim 1, in which the binding agent comprises AU/VWFa-16, a part of a fragment of AU/VWFa-16, or a protein or polypeptide comprising one or more parts of fragments of AU/VWFa-16.

* * * * *

UNITED STATES PATENT AND TRADEMARK OFFICE
CERTIFICATE OF CORRECTION

| | |
|---|---|
| PATENT NO. | : 7,939,277 B2 |
| APPLICATION NO. | : 11/795162 |
| DATED | : May 10, 2011 |
| INVENTOR(S) | : Philip G. de Groot et al. |

It is certified that error appears in the above-identified patent and that said Letters Patent is hereby corrected as shown below:

Col. 25, line 52, should read as follows:

Claim 17. Method according to claim 1, in which the binding agent is a NANOBODY® that specifically binds vWF in the Gplb binding conformation in the presence of vWF in the non-Gplb binding conformation; or a protein or polypeptide that contains one or more NANOBODIES®, in which at least one of said NANOBODIES® is capable of specifically binding vWF in the Gplb binding conformation in the presence of vWF in the non-Gplb binding conformation.

Signed and Sealed this
Fifth Day of July, 2011

David J. Kappos
*Director of the United States Patent and Trademark Office*